(12) United States Patent
Torisawa et al.

(10) Patent No.: US 9,855,394 B2
(45) Date of Patent: Jan. 2, 2018

(54) INSUFFLATION SYSTEM AND INSUFFLATION APPARATUS

(71) Applicants: FUJIFILM Corporation, Tokyo (JP); OSAKA UNIVERSITY, Osaka (JP)

(72) Inventors: Nobuyuki Torisawa, Kanagawa (JP); Manabu Miyamoto, Kanagawa (JP); Kiyokazu Nakajima, Osaka (JP)

(73) Assignees: FUJIFILM Corporation, Tokyo (JP); OSAKA UNIVERSITY, Osaka (JP)

( * ) Notice: Subject to any disclaimer, the term of this patent is extended or adjusted under 35 U.S.C. 154(b) by 288 days.

(21) Appl. No.: 14/682,116

(22) Filed: Apr. 9, 2015

(65) Prior Publication Data

US 2015/0290403 A1 Oct. 15, 2015

(30) Foreign Application Priority Data

Apr. 9, 2014 (JP) .................................. 2014-080255

(51) Int. Cl.
*A61M 13/00* (2006.01)
*A61B 1/267* (2006.01)
(Continued)

(52) U.S. Cl.
CPC ....... *A61M 13/003* (2013.01); *A61B 1/00066* (2013.01); *A61B 1/00131* (2013.01); *A61B 1/015* (2013.01); *A61B 1/267* (2013.01); *A61M 13/00* (2013.01); *A61M 2202/02* (2013.01); *A61M 2202/0225* (2013.01); *A61M 2202/0468* (2013.01); *A61M 2205/3344* (2013.01); *A61M 2205/502* (2013.01); *A61M 2210/1042* (2013.01)

(58) Field of Classification Search
CPC ................ A61M 13/00; A61M 13/003; A61M 2202/02; A61M 2202/0225; A61M 2205/3344
See application file for complete search history.

(56) References Cited

U.S. PATENT DOCUMENTS

2012/0277532 A1* 11/2012 Torisawa ............... A61B 1/015
600/118

FOREIGN PATENT DOCUMENTS

| JP | 2009-131467 | 6/2009 |
| JP | 2012-231897 | 11/2012 |

* cited by examiner

*Primary Examiner* — Nathan R Price
*Assistant Examiner* — Anh Bui
(74) *Attorney, Agent, or Firm* — JCIPRNET

(57) ABSTRACT

There is provided an insufflation system and an insufflation apparatus which can prevent a pressure inside a lumen from rapidly increasing and can achieve operability matched to a sense an operator. The insufflation apparatus is connected to an endoscope and an insertion assisting tool which guides the endoscope into the gastrointestinal tract. Carbon dioxide can be insufflated into a gastrointestinal tract of a patient through an internal conduit of the endoscope according to an operator's operation (manual insufflation). When the operator instructs the insufflation apparatus to perform the automatic insufflation, carbon dioxide is intermittently insufflated into the gastrointestinal tract through the insertion assisting tool so as to make the pressure inside the gastrointestinal tract become a set pressure (automatic insufflation). The insufflation flow rate of the manual insufflation is switched between the high flow rate and the low flow rate according to ON/OFF state of the automatic insufflation.

5 Claims, 16 Drawing Sheets

(51) Int. Cl.
*A61B 1/00* (2006.01)
*A61B 1/015* (2006.01)

INSUFFLATION SYSTEM AND INSUFFLATION APPARATUS

CROSS-REFERENCE TO RELATED APPLICATIONS

The present application claims priority under 35 U.S.C. §119 to Japanese Patent Application No. 2014-080255, filed on Apr. 9, 2014. The above application is hereby expressly incorporated by reference, in its entirety, into the present application.

TECHNICAL FIELD

The present disclosure relates to an insufflation system and an insufflation apparatus, and more particularly to an insufflation system and an insufflation apparatus which enables manual insufflation and automatic insufflation into a lumen of a living body.

DESCRIPTION OF THE BACKGROUND ART

Conventionally, when inspections and treatments are performed using an endoscope, air is insufflated into the lumen through an insufflation conduit provided in the endoscope to secure a field of view of the endoscope and secure an operational area of treatment tools. Air has been mainly used as the gas to be insufflated into the lumen in a conventional art, but carbon dioxide gas ($CO_2$ gas) has been used in recent years. Since carbon dioxide gas has favorable bioabsorbability, there is little damage to the subject (patient). For this reason, there is a tendency for carbon dioxide gas to be used as a gas supply source.

The insufflation system which insufflates gas into the lumen has an advantage in that when carbon dioxide gas is manually insufflated into the lumen according to the operation of an operator, the operator can freely adjust an amount of gas to be insufflated into the lumen according to the intention of the operator, but has a disadvantage in that the operator needs to perform frequent operations in order to keep the pressure inside the lumen constant, thereby increasing an operational burden of the operator.

In view of this, there has been proposed an insufflation system having a function to automatically insufflate carbon dioxide gas into the lumen to make the pressure inside the lumen become a constant pressure (for example, see Japanese Patent Application Laid-Open No. 2009-131467 and No. 2012-231897). The insufflation systems can control the pressure inside the lumen to be stably maintained in a desired state without requiring the operator to perform complicated operations, and hence can reduce the operational burden of the operator.

SUMMARY

By the way, there has been a need to develop an insufflation system which enables manual insufflation and automatic insufflation. The insufflation system can manually insufflate air into the lumen according to the operation of the operator while automatically insufflating air so that the pressure inside the lumen becomes a predetermined pressure, thereby allowing the operational burden of the operator to be reduced and allowing the pressure inside the lumen to be finely adjusted according to the intention of the operator, and thus improving convenience.

However, in a case where an insufflation flow rate (volume of gas insufflated per unit time) in the manual insufflation is set to be greater than the insufflation flow rate in the automatic insufflation in the above described insufflation system, when the manual insufflation is performed while the automatic insufflation into the lumen is performed, the above described insufflation system has a problem that a pressure inside the lumen is rapidly increased, resulting in increase of the burden on the patient. Thus, the operator may feel that the system has too high response sensitivity and poor operability.

Meanwhile, in a case where the insufflation flow rate in the manual insufflation is set to be less than the insufflation flow rate in the automatic insufflation, when only the manual insufflation is performed without performing the automatic insufflation, it takes longer time to adjust the pressure inside the lumen. In this case, the operator may feel that the system has low response sensitivity and poor operability.

Particularly when a lumen such as the stomach and large intestine is insufflated, finer operations may be required than when a body cavity such as the abdomen is insufflated. Therefore, even when the manual insufflation and the automatic insufflation are used concurrently, the operability matched to the sense of the operator is highly required.

Japanese Patent Application Laid-Open No. 2009-131467 and No. 2012-231897 disclose the insufflation system having a function to automatically insufflate carbon dioxide gas into the lumen to make the pressure inside the lumen become a predetermined pressure, but do not pay attention to the aforementioned problems, nor do they mention any means for solving the problems.

In view of the above circumstances, the present disclosure has been made, and the present disclosure provides an insufflation system and an insufflation apparatus which enables to perform manual insufflation and automatic insufflation into a lumen of a living body while preventing the pressure inside the lumen from rapidly increasing and can achieve operability matched to the sense of the operator.

In order to solve the above problems, an insufflation system according to an aspect of the present disclosure, which insufflates a gas supplied from a gas supply source into a lumen of a living body, the insufflation system comprising: a first insufflation conduit through which the gas is automatically insufflated into the lumen; a second insufflation conduit through which the gas is insufflated into the lumen by manual operation; a pressure detecting device configured to detect a pressure inside the lumen; a control device configured to control an insufflation flow rate of the first insufflation conduit based on a pressure difference between the pressure detected by the pressure detecting device and a preset set pressure; a determination device configured to determine whether or not the gas is insufflated through the first insufflation conduit; and a flow rate switching device configured to selectively switch an insufflation flow rate of the gas insufflated through the second insufflation conduit between a first insufflation flow rate $MF_1$ and a second insufflation flow rate $MF_2$ greater than the first insufflation flow rate $MF_1$ according to a determination result of the determination device.

According to the aspect, the insufflation flow rate of the gas insufflated through the second insufflation conduit is selectively switched between the first insufflation flow rate $MF_1$ and the second insufflation flow rate $MF_2$ greater than the first insufflation flow rate $MF_1$ according to whether or not the gas insufflated through the first insufflation conduit. This makes it possible to prevent the pressure inside the lumen from rapidly increasing and to achieve operability matched to a sense of the operator even when automatic insufflation and manual insufflation are used concurrently.

In the insufflation system according to an aspect of the present disclosure, it is preferable that when the gas is insufflated through the first insufflation conduit, the flow rate switching device switches the insufflation flow rate of the gas insufflated through the second insufflation conduit to the first insufflation flow rate $MF_1$.

According to the aspect, when the automatic insufflation is performed, the insufflation flow rate of the manual insufflation is switched to a low flow rate. Thus, even when the automatic insufflation and the manual insufflation are used concurrently, the pressure inside the lumen can be easily fine-adjusted by the manual insufflation, and the lumen can be easily maintained in an appropriate expanded condition. This makes it possible to prevent the pressure inside the lumen from rapidly increasing and to achieve operability matched to a sense of the operator.

In the insufflation system according to an aspect of the present disclosure, it is preferable that when AF is defined as the insufflation flow rate of the gas insufflated through the first insufflation conduit, a following expression is satisfied.

$$MF_1 < AF \leq MF_2$$

According to the aspect, the insufflation flow rate (AF) of the gas insufflated through the first insufflation conduit is set to be less than or equal to the second insufflation flow rate ($MF_2$) so as to make it possible to insufflate the gas into the lumen with a sense as close to the manual insufflation when only the automatic insufflation is performed. Further, the insufflation flow rate (AF) of the gas insufflated through the first insufflation conduit is set to be greater than the first insufflation flow rate ($MF_1$) so as to make it possible to easily fine-adjust the pressure inside the lumen by the manual insufflation while preventing the pressure inside the lumen from rapidly increasing and to easily maintain the lumen in an appropriate expanded condition, even in the concurrent use of the manual insufflation during the automatic insufflation.

In the insufflation system according to an aspect of the present disclosure, it is preferable that when AF is defined as the insufflation flow rate of the gas insufflated through the first insufflation conduit, a following expression is satisfied.

$$MF_1 + AF \leq MF_2$$

According to the aspect, even when the manual insufflation is concurrently used during the automatic insufflation, the entire insufflation flow rate ($MF_1+AF$) of the gas insufflated into the lumen is less than or equal to the insufflation flow rate ($MF_2$) when only the manual insufflation is performed. Thus, even when the manual insufflation and the automatic insufflation are concurrently used, the pressure inside the lumen is prevented from rapidly increasing, and operability matched to a sense of the operator can be achieved.

In the insufflation system according to an aspect of the present disclosure, it is preferable that the control device alternately repeats an insufflation step of insufflating the gas through the first insufflation conduit, and a pressure detection step of stopping insufflating the gas and detecting the pressure inside the lumen by the pressure detecting device.

According to the aspect, the automatic insufflation into the lumen is intermittently performed and the pressure inside the lumen is detected while the automatic insufflation is stopped, which can stabilize the automatic insufflation into the lumen.

An insufflation apparatus according to another aspect of the present disclosure, which insufflates a gas supplied from a gas supply source into a lumen of a living body, the insufflation apparatus comprising: a pressure detecting device configured to detect a pressure inside the lumen; a control device configured to control an insufflation flow rate of the gas supplied to a first external conduit which is connected to the insufflation apparatus and through which the gas is automatically insufflated into the lumen, based on a pressure difference between the pressure detected by the pressure detecting device and a preset set pressure; a determination device configured to determine whether or not the gas is supplied to the first external conduit; and a flow rate switching device configured to selectively switch an insufflation flow rate of the gas supplied to the second external conduit which is connected to the insufflation apparatus and through which the gas is insufflated into the lumen by manual operation, between a first insufflation flow rate $MF_1$ and a second insufflation flow rate $MF_2$ greater than the first insufflation flow rate $MF_1$ according to a determination result of the determination device.

The present disclosure can achieve operability matched to a sense of the operator while preventing the pressure inside the lumen from rapidly increasing.

DESCRIPTION OF THE EXEMPLARY EMBODIMENTS

Hereinafter, a preferable embodiment of the present disclosure will be described in detail with reference to the accompanying drawings.

Figure 1:
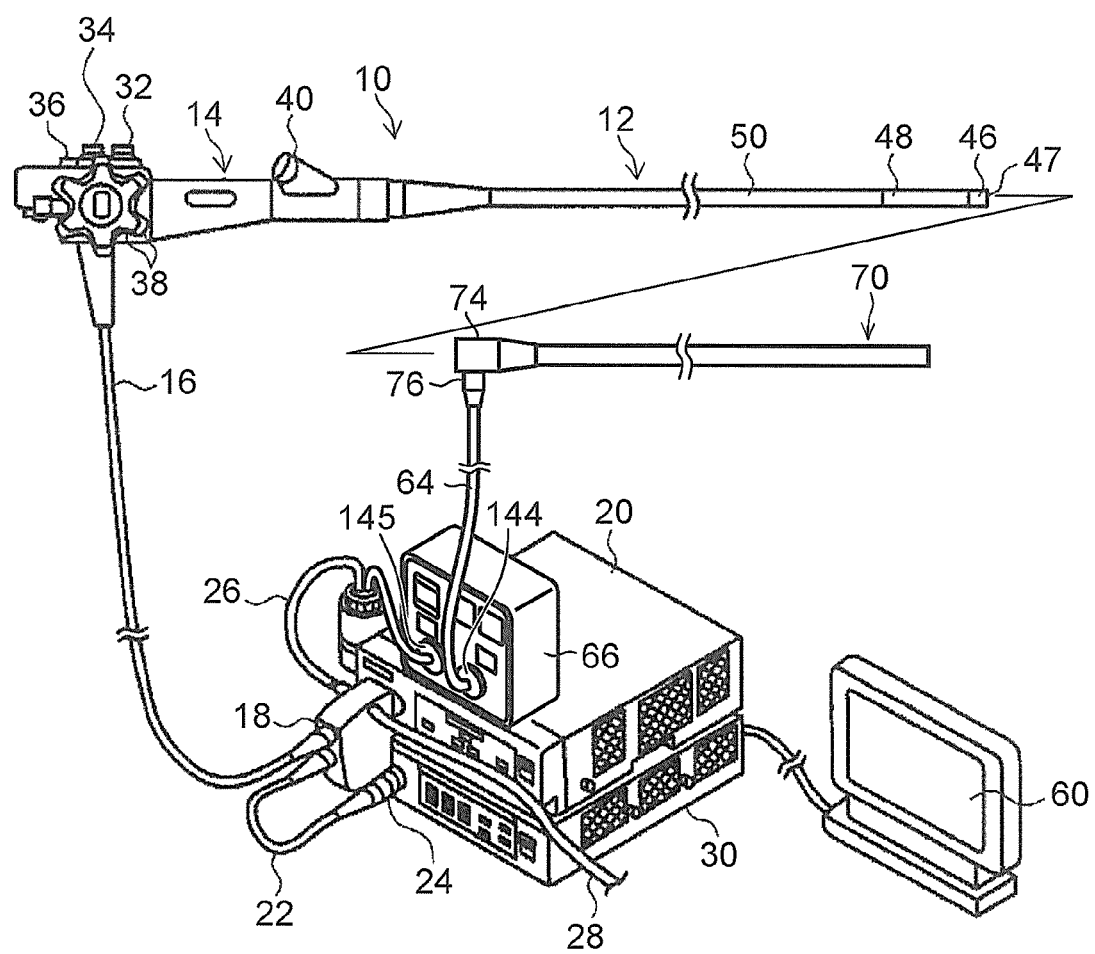
FIG. 1 is an entire configuration diagram illustrating a schematic configuration of an insufflation system according to an embodiment of the present disclosure.

FIG. 1 is an entire configuration diagram illustrating a schematic configuration of an insufflation system according to an embodiment of the present disclosure. The insufflation system illustrated in FIG. 1 mainly includes an endoscope 10, an insertion assisting tool 70, a light source apparatus 20, a processor 30, and an insufflation apparatus 66.

The endoscope 10 includes an insertion portion 12 which is inserted into a lumen of a patient, for example, a gastrointestinal tract such as a stomach and large intestine of a patient; and a hand operating unit 14 which is continuously connected to the insertion portion 12. A universal cable 16 is connected to the hand operating unit 14. An LG (Light Guide) connector 18 is provided at a distal end of the universal cable 16. Illumination light can be transmitted to an illumination optical system 54 to be described later (see FIG. 2) by detachably connecting the LG connector 18 to the light source apparatus 20. An electrical connector 24 is connected to the LG connector 18 through a cable 22, and the electrical connector 24 is detachably connected to the processor 30. Note that a tube 26 for air/water insufflation and a tube 28 for suction are also connected to the LG connector 18.

The hand operating unit 14 includes an air/water insufflation button 32, a suction button 34, and a shutter button 36, which are arranged side by side, as well as a pair of angle knobs 38 and 38, and a forceps insertion portion 40.

Meanwhile, the insertion portion 12 includes a distal end portion 46, a curved portion 48, and a flexible portion 50. The curved portion 48 is remotely bent by rotating the pair of angle knobs 38 and 38 provided in the hand operating unit 14. This makes it possible to direct a distal end surface 47 of the distal end portion 46 in a desired direction.

Figure 2:
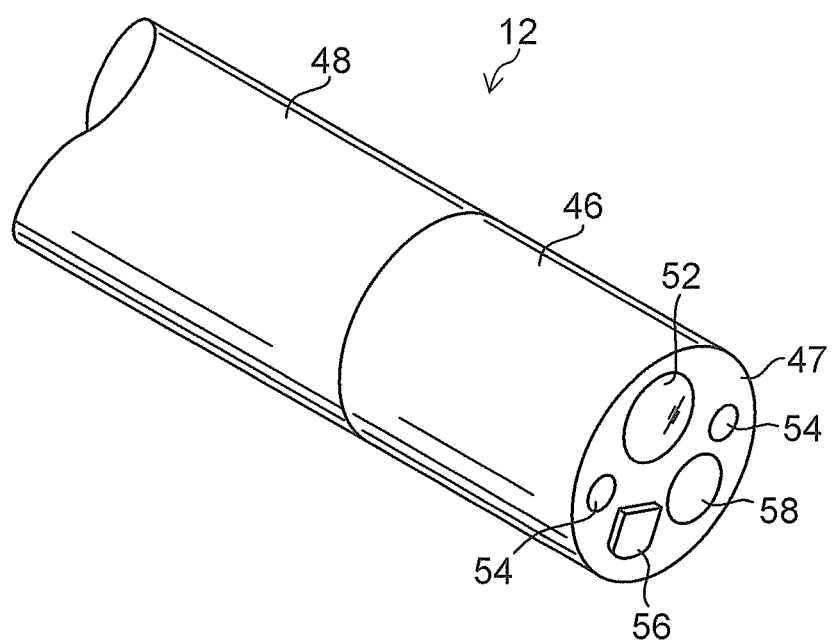
FIG. 2 is perspective view illustrating a distal end portion of an insertion portion of an endoscope.

As illustrated in FIG. 2, the distal end surface 47 of the distal end portion 46 includes an observation optical system 52, illumination optical systems 54 and 54, an air/water insufflation nozzle 56, and a forceps port 58. A CCD (Charge Coupled Device) (unillustrated) is disposed rearward of the observation optical system 52. A signal cable is connected to a substrate which supports the CCD. The signal cable is inserted into the insertion portion 12, the hand operating unit 14, and the universal cable 16 in FIG. 1, and extends up to the electrical connector 24 to be connected to the processor 30. Thus, an observed image captured by the observation optical system 52 in FIG. 2 is formed on a light receiving surface of the CCD, in which the image is converted to an electrical signal. The electrical signal is outputted to the processor 30 in FIG. 1 through the signal cable, and then converted to a video signal. Thus, the observed image is displayed on a monitor 60 connected to the processor 30.

An exit end of a light guide (unillustrated) is disposed rearward of the illumination optical systems 54 and 54 in FIG. 2. The light guide is inserted into the insertion portion 12, the hand operating unit 14, and the universal cable 16 in FIG. 1. An incident end of the light guide is disposed at a light guide rod 19 (see FIG. 3) of the LG connector 18. When the light guide rod 19 of the LG connector 18 is connected to the light source apparatus 20, illumination light emitted from the light source apparatus 20 is transmitted to the illumination optical systems 54 and 54 through the light guide, and then the illumination light is emitted from the illumination optical systems 54 and 54.

The insertion assisting tool 70 is used to guide the insertion portion 12 of the endoscope 10 into a gastrointestinal tract. The insertion assisting tool 70 is a tubular body having sufficient flexibility and includes an insertion channel 68 (see FIG. 3) penetrating from the proximal end to the distal end. The inner diameter of the insertion assisting tool 70, that is, the diameter of the insertion channel 68, is slightly larger than the outer diameter of the insertion portion 12, and hence the insertion assisting tool 70 is large enough to insert the insertion portion 12 thereinto.

When the insertion portion 12 of the endoscope 10 is inserted into the gastrointestinal tract, the insertion portion 12 is inserted into the insertion channel 68 of the insertion assisting tool 70 so as to be disposed in a state in which the insertion assisting tool 70 covers the outer peripheral surface of the insertion portion 12.

In addition, the proximal end of the insertion assisting tool 70 includes a rigid grip portion 74. The proximal end surface of the grip portion 74 includes an opening for inserting the insertion portion 12 of the endoscope 10 into the insertion channel 68 of the insertion assisting tool 70. The outer peripheral surface of the grip portion 74 includes a gas supply port 76 for supplying carbon dioxide gas. The gas supply port 76 is connected to the insufflation apparatus 66 through an automatic insufflation tube 64. Note that the automatic insufflation tube 64 corresponds to a first external conduit.

Here, the description focuses on the conduit configuration of the endoscope 10 and the insertion assisting tool 70.

Figure 3:
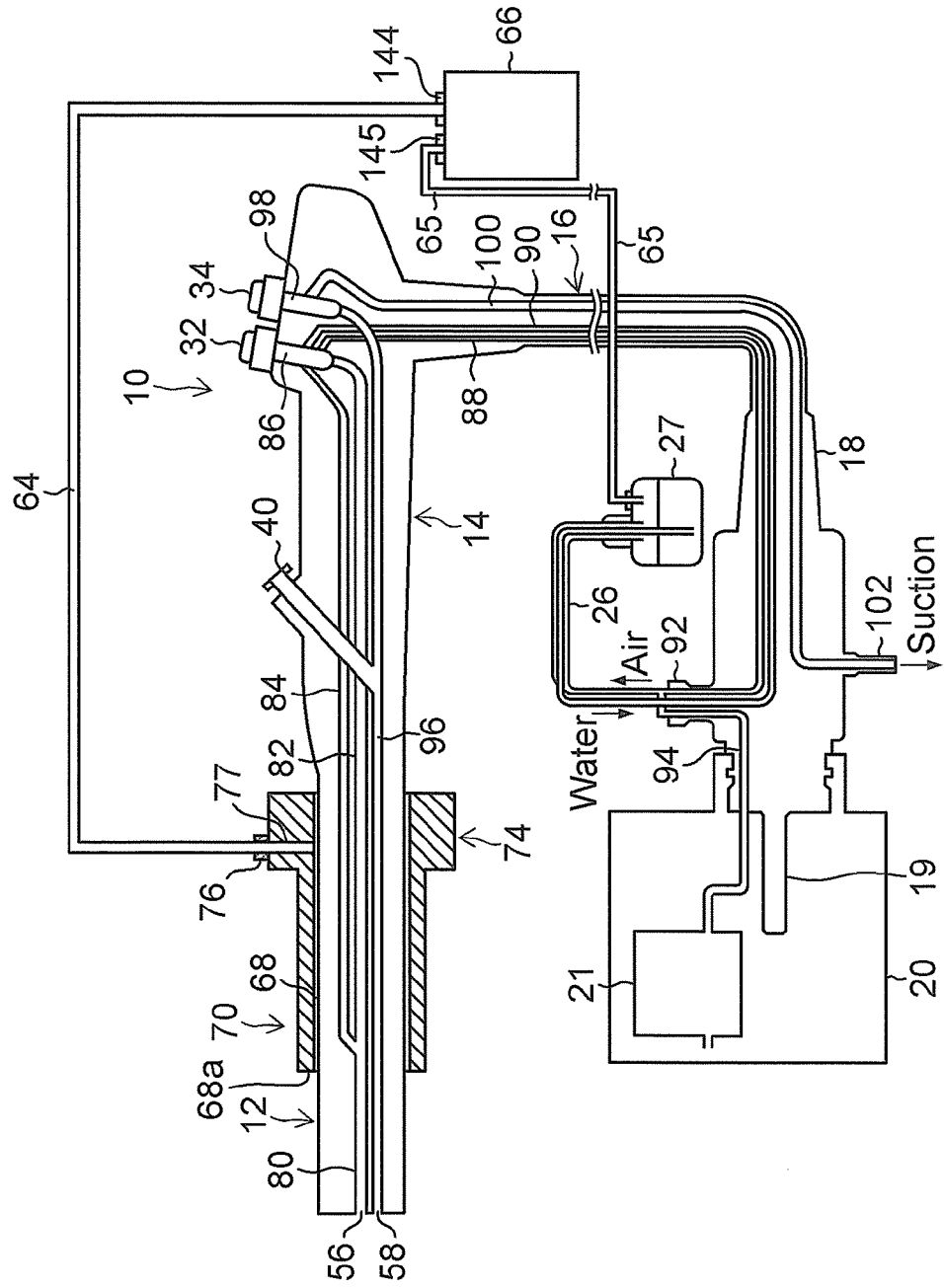
FIG. 3 is a configuration diagram schematically illustrating a conduit configuration of the endoscope and an insertion assisting tool.

FIG. 3 is a configuration diagram schematically illustrating the conduit configuration of the endoscope 10 and the insertion assisting tool 70. As illustrated in FIG. 3, an air/water insufflation tube 80 is connected to an air/water insufflation nozzle 56 provided at the distal end surface 47 of the insertion portion 12. The air/water insufflation tube 80 is branched into an insufflation tube 82 and a water insufflation tube 84, each of which is connected to a valve 86 disposed in the hand operating unit 14. An air supply tube 88 and a water supply tube 90 are connected to the valve 86, to which an air/water insufflation button 32 is attached. In a state in which the air/water insufflation button 32 is projected, the insufflation tube 82 communicates with the air supply tube 88. When the air/water insufflation button 32 is pressed down, the water insufflation tube 84 communicates with the water supply tube 90. The air/water insufflation button 32 includes a vent (unillustrated), through which the air supply tube 88 communicates with the outside air.

The air supply tube 88 and the water supply tube 90 are inserted into the universal cable 16, and extend up to a water insufflation connector 92 of the LG connector 18. A tube 26 is detachably connected to the water insufflation connector 92. The distal end of the tube 26 is connected to a water storage tank 27. The water supply tube 90 communicates below a liquid surface of the water storage tank 27, and the air supply tube 88 communicates above the liquid surface of the water storage tank 27.

An air tube 94 is connected to the water insufflation connector 92. The air tube 94 communicates with the air supply tube 88. In addition, the LG connector 18 is connected to the light source apparatus 20, thereby communicating the air tube 94 with an air pump 21 inside the light source apparatus 20.

Thus, when the air pump 21 is driven to blow air, the air is delivered to the air supply tube 88 through the air tube 94. While the air/water insufflation button 32 is not operated, the air escapes to the outside through the vent (unillustrated). When the operator closes the vent, the air is passed from the air supply tube 88 to the insufflation tube 82 and is jetted from the air/water insufflation nozzle 56. When the operator presses down the air/water insufflation button 32, the air supply tube 88 is disconnected from the insufflation tube 82, and then the air fed into the air tube 94 is supplied above the liquid surface of the water storage tank 27. This increases the internal pressure of the water storage tank 27 to cause water to be supplied to the water supply tube 90. Then, the water is delivered to the water insufflation tube 84 and is jetted from the air/water insufflation nozzle 56. Thus, the observation optical system 52 is cleaned by jetting water or air from the air/water insufflation nozzle 56 onto the observation optical system 52.

A forceps tube 96 is connected to the forceps port 58 provided on the distal end surface 47 of the insertion portion 12. The forceps tube 96 is branched into two: one communicating with a forceps insertion portion 40 and the other communicating with a valve 98. Thus, when a treatment tool such as a forceps is inserted from the forceps insertion portion 40, the treatment tool can be introduced from the forceps port 58.

A suction tube 100 is connected to the valve 98, and a suction button 34 is attached to the valve 98. In a state in which the suction button 34 is projected, the suction tube 100 communicates with the outside air. When the suction button 34 is pressed, the suction tube 100 is connected to the forceps tube 96.

The suction tube 100 extends up to a suction connector 102 of the LG connector 18. When the tube 28 (see FIG. 1) is connected to the suction connector 102, the suction tube 100 communicates with an unillustrated suction apparatus. Thus, when the suction button 34 is pressed in a state in which the suction apparatus is driven, a lesion part, or the like can be sucked through the forceps port 58.

In addition, one end of the manual insufflation tube 65 is detachably connected to the water storage tank 27 and communicates above the liquid surface of the water storage tank 27. The other end of the manual insufflation tube 65 is connected to a manual insufflation connector 145 of the insufflation apparatus 66. Thus, carbon dioxide is supplied from the manual insufflation connector 145 of the insufflation apparatus 66 to the water storage tank 27 through the manual insufflation tube 65. In the same manner as when air is supplied from the air pump 21 of the light source apparatus 20 to the air supply tube 88, water or carbon dioxide is jetted from the air/water insufflation nozzle 56 according to the operation of the air/water insufflation button 32 by the operator. Note that the manual insufflation tube 65 corresponds to the second external conduit.

Note that it is preferable that a control device (unillustrated) for alternatively controlling these drive operations is provided to prevent simultaneous supply of carbon dioxide from the insufflation apparatus 66 and air from the air pump 21 to the air supply tube 88. For example, the control device is provided in the light source apparatus 20, the insufflation apparatus 66, or the processor 30 and performs control so that the carbon dioxide supplied from the insufflation apparatus 66 takes priority over the air supplied from the air pump 21. In this case, the air pump 21 is used as a spare gas supply source when a carbon dioxide cylinder 110 is exhausted.

As described above, "manual insufflation" in the present description is defined as insufflating carbon dioxide into the gastrointestinal tract from the insufflation apparatus 66 in response to manual operation by an operator who manually operates a predetermined manual operation member such as the air/water insufflation button 32 of the endoscope 10.

Meanwhile, one end of the automatic insufflation tube 64 is detachably connected to the gas supply port 76 provided in the grip portion 74 of the insertion assisting tool 70, and the other end of the automatic insufflation tube 64 is connected to an automatic insufflation connector 144 of the insufflation apparatus 66.

The gas supply port 76 provided in the grip portion 74 of the insertion assisting tool 70 communicates with the insertion channel 68 inside the insertion assisting tool 70 through a conduit 77 formed in the grip portion 74. In a state in which the insertion portion 12 is inserted into the insertion channel 68, a gap is formed between the inner peripheral surface of the insertion assisting tool 70 and the outer peripheral surface of the insertion portion 12, and the gap forms a distal end opening portion 68a at the distal end of the insertion assisting tool 70. Thus, the gas supply port 76 communicates with the distal end opening portion 68a through the conduit 77 and the insertion channel 68 (gap).

Thus, the carbon dioxide is supplied from the automatic insufflation connector 144 of the insufflation apparatus 66 to the insertion channel 68 through the automatic insufflation tube 64 and the conduit 77, and then introduced from the distal end opening portion 68a of the insertion channel 68 into the gastrointestinal tract.

Note that although not illustrated, a valve member as an airtight holding device which holds airtightness in close contact with an outer periphery of the insertion portion 12 of the endoscope 10 is provided near an opening of the insertion channel 68 on the proximal end side of the grip portion 74 of the insertion assisting tool 70 to prevent the carbon dioxide insufflated into the gastrointestinal tract from flowing out of the body through the insertion channel 68. Thus, the carbon dioxide supplied from the insufflation apparatus 66 to the insertion channel 68 of the insertion assisting tool 70 is insufflated from the distal end opening portion 68a into the gastrointestinal tract without flowing out of the body through the insertion channel 68.

As described above, "automatic insufflation" in the present description is defined as automatically insufflating carbon dioxide from the insufflation apparatus 66 into the gastrointestinal tract without the operator to manually operate a predetermined manual operation member.

Now, the description focuses on the configuration of the insufflation apparatus 66.

Figure 4:
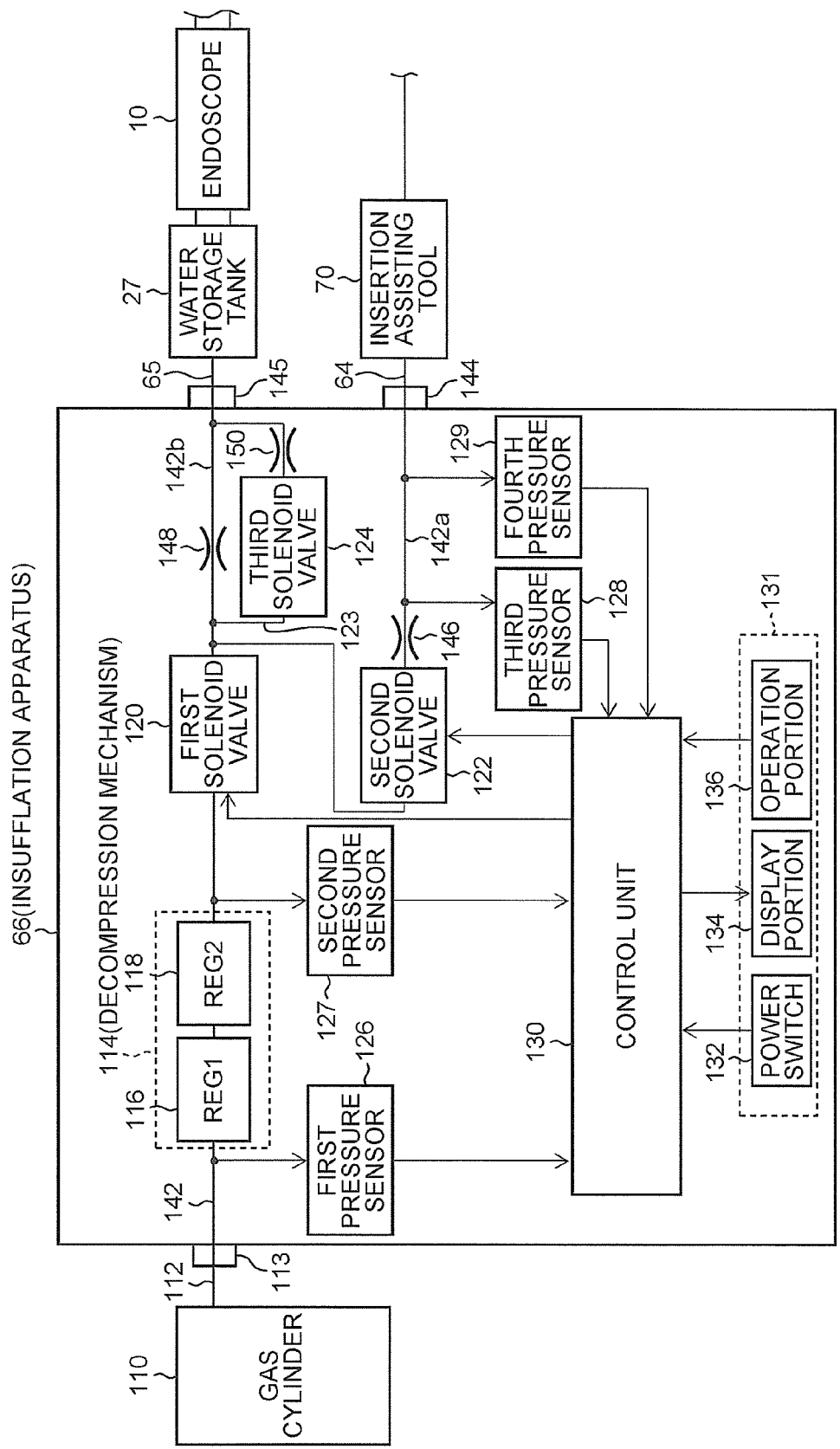
FIG. 4 is a block diagram illustrating a configuration of an insufflation apparatus.

FIG. 4 is a block diagram illustrating the configuration of the insufflation apparatus 66.

As described below, the insufflation apparatus 66 has a function to insufflate carbon dioxide for manual insufflation from the manual insufflation connector 145 through an internal insufflation conduit. As illustrated in FIGS. 1 and 3, when the manual insufflation connector 145 is connected to the water storage tank 27 through the manual insufflation tube 65, the insufflation conduit is connected to the water storage tank 27 and the endoscope 10 and then to an insufflation conduit through which carbon dioxide is insufflated into the gastrointestinal tract. Thus, the insufflation system of the present embodiment includes the insufflation conduit (second insufflation conduit) for manual insufflation through which carbon dioxide is insufflated into the gastrointestinal tract according to a manual operation of the air/water insufflation button 32 of the endoscope 10.

As described below, the insufflation apparatus 66 also has a function to insufflate carbon dioxide for automatic insufflation from the automatic insufflation connector 144 through an internal insufflation conduit. As illustrated in FIGS. 1 and 3, when the automatic insufflation connector 144 is connected to the insertion assisting tool 70 through the automatic insufflation tube 64, the insufflation conduit is connected to the insertion assisting tool 70 and then to an insufflation conduit through which carbon dioxide is insufflated into the gastrointestinal tract. Thus, the insufflation system of the present embodiment includes the insufflation conduit (first insufflation conduit) for automatic insufflation through which carbon dioxide is automatically insufflated into the gastrointestinal tract.

As illustrated in FIG. 4, the insufflation apparatus 66 includes a decompression mechanism 114, first to third solenoid valves 120, 122, and 124, first to fourth pressure sensors 126, 127, 128, and 129, a control unit 130, and a front panel (operation panel) 131.

One end of a high-pressure hose 112 is detachably connected to a high pressure connector 113 of the insufflation apparatus 66, and the other end thereof is connected to a carbon dioxide cylinder 110 as a gas supply source. In other words, the insufflation apparatus 66 communicates with the carbon dioxide cylinder 110 through the high-pressure hose 112. Thus, carbon dioxide is supplied from the carbon dioxide cylinder 110 to the insufflation apparatus 66 through the high-pressure hose 112 and the high pressure connector 113. Note that the gas supply source which supplies carbon dioxide to the insufflation apparatus 66 may be other than the carbon dioxide cylinder 110.

The high pressure connector 113 is connected to one end of an internal conduit 142 provided inside the insufflation apparatus 66. The internal conduit 142 is connected to a decompression mechanism 114 for decompressing the carbon dioxide supplied from the carbon dioxide cylinder 110 to a predetermined pressure. An exit side of the decompression mechanism 114 (side opposite to the high pressure connector 113) is branched into two conduits 142a and 142b (hereinafter referred to as a first branch conduit 142a and a second branch conduit 142b).

The decompression mechanism 114 is a decompression device which gradually reduces the pressure of the carbon dioxide supplied from the carbon dioxide cylinder 110, to a proper pressure. The decompression mechanism 114 includes two regulators (decompression valves) 116 and 118 which are arranged in series. For example, the first regulator 116 reduces the pressure of the carbon dioxide supplied from the carbon dioxide cylinder 110, from 10 MPa to 0.6 MPa. Then, the second regulator 118 reduces the pressure of the carbon dioxide reduced by the first regulator 116, from 0.6 MPa to 0.05 MPa.

The first pressure sensor 126 is a pressure detecting device which detects the pressure of the carbon dioxide supplied from the carbon dioxide cylinder 110. The first pressure sensor 126 is connected to the internal conduit 142 between the high pressure connector 113 and the decompression mechanism 114. The detection result of the first pressure sensor 126 is outputted to the control unit 130.

The second pressure sensor 127 is a pressure detecting device which detects the pressure of the carbon dioxide reduced by the decompression mechanism 114. The second pressure sensor 127 is connected to the internal conduit 142 between the decompression mechanism 114 and the first solenoid valve 120. The detection result of the second pressure sensor 127 is outputted to the control unit 130.

The first solenoid valve 120 is an opening and closing device which can communicate with and interrupt the internal conduit 142. The first solenoid valve 120 is disposed closer to a downstream side than the decompression mechanism 114 in the internal conduit 142 and closer to an upstream side than a branch portion at which the internal conduit 142 is branched into the branch conduits 142a and 142b. The first solenoid valve 120 is opened or closed based on a control signal outputted from the control unit 130. The opening or closing of the first solenoid valve 120 causes the internal conduit 142 to be communicated or interrupted, which collectively supplies or does not supply the carbon dioxide to each of the branch conduits 142a and 142b.

Note that an open state of the first solenoid valve 120 is defined as a state in which the first solenoid valve 120 causes the conduit to be communicated and a closed state thereof is defined as a state in which the first solenoid valve 120 causes the conduit to be interrupted. Note also that the open state and the closed state of the second solenoid valve 122 and the third solenoid valve 124 are also defined in the same manner as above.

The first branch conduit 142a constitutes part of the insufflation conduit (first insufflation conduit) for automatic insufflation, and one end of the first branch conduit 142a is connected to the automatic insufflation connector 144. The second solenoid valve 122 is disposed on an upstream side of the first branch conduit 142a (a branch portion side of the internal conduit 142).

The second solenoid valve 122 is an opening and closing device which can communicate with and interrupt the first branch conduit 142a. The second solenoid valve 122 is opened or closed based on a control signal outputted from the control unit 130, switching to an open state of communicating with the first branch conduit 142a and a closed state of interrupting the first branch conduit 142a.

The first branch conduit 142a includes a first orifice 146 (throttle portion) as a first flow rate restricting device which is disposed closer to a downstream side than the second solenoid valve 122. The first orifice 146 has a smaller effective opening area of the conduit than that on the upstream side and the downstream side of the first orifice 146, thereby restricting the flow rate of carbon dioxide flowing in the first branch conduit 142a, that is, the insufflation flow rate of carbon dioxide in the automatic insufflation.

Note that the effective opening area of the conduit refers to an area of the cross section perpendicular to the axis of the conduit. When the conduit has a circular cross section, the effective opening area of the conduit is found by multiplying the circumference ratio (pi) times the radius squared.

The third pressure sensor 128 and the fourth pressure sensor 129 are pressure detecting devices which detect a pressure inside the gastrointestinal tract through the insufflation conduit (the first branch conduit 142a, the automatic insufflation tube 64, and the insertion assisting tool 70) for insufflating carbon dioxide into the gastrointestinal tract. The third pressure sensor 128 and the fourth pressure sensor 129 are disposed closer to a downstream side than the first orifice 146 in the first branch conduit 142a. The detection result of each of the pressure sensors 128 and 129 is outputted to the control unit 130.

The present embodiment uses any one of the third pressure sensor 128 and the fourth pressure sensor 129 as a main sensor and the other as a spare sensor. Thus, even when the main sensor fails, the spare sensor can be used instead to detect a pressure inside the gastrointestinal tract, thereby improving the reliability of pressure detection inside the gastrointestinal tract.

Note that if the difference between the pressure detected by the third pressure sensor 128 and the pressure detected by the fourth pressure sensor 129 exceeds a predetermined value, it can be judged that any one of the pressure sensors fails. In addition, as the third pressure sensor 128 and the fourth pressure sensor 129, pressure sensors having at least one different characteristic in pressure measurement range, withstanding pressure, and resolution may be used to prevent the two pressure sensors from failing at the same time. Further, such pressure sensors having different characteristics may be used to achieve both higher resolution and wider pressure measurement range than by using only each pressure sensor for pressure detection.

The second branch conduit 142b constitutes part of the insufflation conduit (second insufflation conduit) for manual insufflation, and one end of the second branch conduit 142b is connected to the manual insufflation connector 145. The second branch conduit 142b includes a second orifice 148 (throttle portion) as the second flow rate restricting device. In addition, a bypass conduit 123 which bypasses the second orifice 148 is connected to the second branch conduit 142b. A third solenoid valve 124 is disposed on the way of the bypass conduit 123, and a third orifice 150 (throttle portion) as the third flow rate restricting device is disposed on the downstream side of the third solenoid valve 124.

The second orifice 148 has a smaller effective opening area of the conduit than that on the upstream side and the downstream side of the second orifice 148, thereby restricting the flow rate of carbon dioxide flowing in the second branch conduit 142b without passing through the bypass conduit 123.

The third orifice 150 has a smaller effective opening area of the conduit than that on the upstream side and the downstream side of the third orifice 150, and restricts the flow rate of carbon dioxide flowing in the bypass conduit 123. Note that the effective opening area of the first to third orifices 146, 148, and 150 as the first to third flow rate restricting devices may be fixed or variable. Note also that the first to third flow rate restricting devices may restrict the insufflation flow rate by means other than the orifice.

The third solenoid valve 124 is an opening and closing device which can communicate with and interrupt the bypass conduit 123. The third solenoid valve 124 is opened or closed based on a control signal outputted from the control unit 130, switching between the open state of communicating with the bypass conduit 123 and the closed state of interrupting the bypass conduit 123. As the third solenoid valve 124 is switched between the open state and the closed state, the insufflation flow rate of the carbon dioxide which can be insufflated from the manual insufflation connector 145 is switched in two steps.

When the third solenoid valve 124 is in the open state, a state is attained in which the carbon dioxide can be insufflated from the manual insufflation connector 145 at a high flow rate obtained by combining the carbon dioxide passed through the second orifice 148 and the carbon dioxide passed through the third orifice 150 on the bypass conduit 123.

Meanwhile, when the third solenoid valve 124 is in the closed state, because the carbon dioxide does not flow through the bypass conduit 123, a state is attained in which the carbon dioxide passed through only the second orifice 148 can be insufflated from the manual insufflation connector 145 at a low flow rate.

The front panel (operation panel) 131 is disposed in front of a housing constituting the insufflation apparatus 66. The front panel 131 includes a power switch 132, a display portion 134, and an operation portion 136, each of which is connected to the control unit 130.

Figure 5:
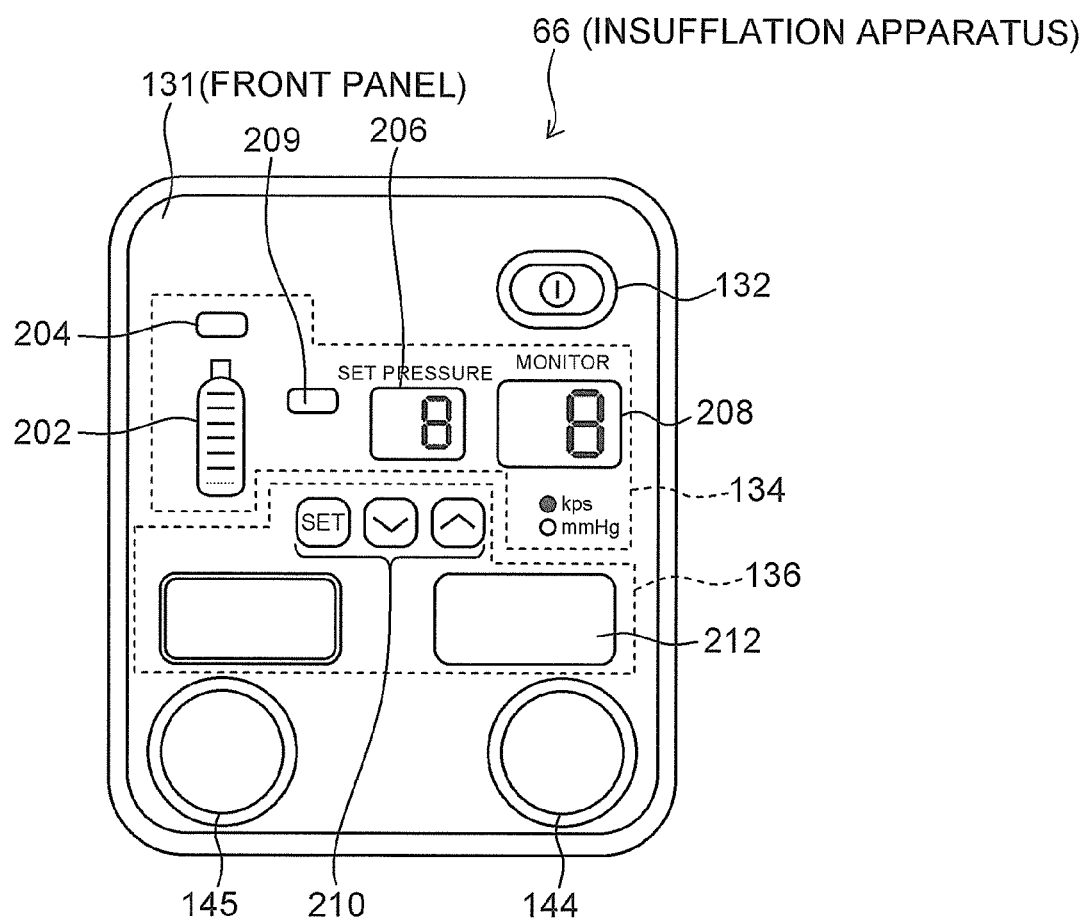
FIG. 5 is a diagram illustrating a front panel of the insufflation apparatus.

FIG. 5 is a diagram illustrating the front panel 131 of the insufflation apparatus 66. As illustrated in FIG. 5, the display portion 134 includes: a remaining amount display portion 202 which displays the remaining amount of carbon dioxide of the carbon dioxide cylinder 110; a gas warning display portion 204 which displays a warning when the remaining amount of carbon dioxide is less than or equal to a predetermined level; a set pressure display portion 206 which displays a set pressure inside the gastrointestinal tract; a pressure display portion 208 which displays a pressure (current pressure) inside the gastrointestinal tract; and a pressure warning display portion 209 which displays a warning when the pressure inside the gastrointestinal tract exceeds the set pressure.

The operation portion 136 includes: a pressure setting portion 210 for setting a set pressure inside the gastrointestinal tract; and an automatic insufflation button 212 for selecting ON (execution) or OFF (stop) of the automatic insufflation, and the like. When each portion of the operation portion 136 is operated, an operation signal corresponding to the operation is outputted to the control unit 130.

Now, by referring back to FIG. 4, the control unit 130 performs entire control of the insufflation apparatus 66 and includes a CPU (Central Processing Unit), a memory, and the like, all of which are not illustrated. The memory stores control programs for operating the insufflation apparatus 66 and various set information (such as a set pressure inside the gastrointestinal tract set by the pressure setting portion 210).

The control unit 130 displays the remaining amount of carbon dioxide of the carbon dioxide cylinder 110 on the remaining amount display portion 202 based on the detection result of the first pressure sensor 126. When the remaining amount of carbon dioxide is less than or equal to a predetermined level, the control unit 130 causes the gas warning display portion 204 to display a warning and at the same time generates an alarm. This makes it possible to replace the carbon dioxide cylinder 110 with a new one before the carbon dioxide is exhausted.

In addition, the control unit 130 displays the pressure inside the gastrointestinal tract on the pressure display portion 208 based on the detection result of the third pressure sensor 128 or the fourth pressure sensor 129 as the pressure detecting device, and at the same time displays the set pressure inside the gastrointestinal tract set by the pressure setting portion 210, on the set pressure display portion 206.

Further, the control unit 130 switches the setting between ON (execution) and OFF (stop) of the automatic insufflation according to the pressing operation of the automatic insufflation button 212.

The automatic insufflation button 212 is linked with, for example, an automatic return type switch. The control unit 130 detects whether or not the automatic insufflation button is pressed down, according to an operation signal which changes depending on the state of the switch. When it is detected that the automatic insufflation button is pressed down in a state in which the automatic insufflation is set to OFF, the control unit 130 sets the automatic insufflation to ON until it is detected that the automatic insufflation button is pressed down again. When it is detected that the automatic insufflation button is pressed down in a state in which the automatic insufflation is set to ON, the control unit 130 sets the automatic insufflation to OFF until it is detected that the automatic insufflation button is pressed down again.

Note that the control unit 130 includes a determination device which determines ON/OFF of the automatic insufflation, and the determination device which determines ON/OFF of the automatic insufflation may not be necessarily configured as the automatic insufflation button 212 like the present embodiment.

When the automatic insufflation is set to ON, the control unit 130 serves as a control device which controls the insufflation flow rate in the automatic insufflation. More specifically, the control unit 130 controls the opening and closing of the second solenoid valve 122 to supply carbon dioxide from the automatic insufflation connector 144 through the first branch conduit 142a so that the pressure inside the gastrointestinal tract becomes the set pressure inside the gastrointestinal tract set by the pressure setting portion 210. Then, the carbon dioxide is insufflated into the gastrointestinal tract through the automatic insufflation tube 64 and the insertion assisting tool 70.

When the automatic insufflation is set to OFF, the control unit 130 controls the second solenoid valve 122 to be in a closed state to prevent carbon dioxide from being supplied from the automatic insufflation connector 144.

Meanwhile, it is set that carbon dioxide can be constantly supplied from the manual insufflation connector 145 through the second branch conduit 142b. The operator can operate the air/water insufflation button 32 of the endoscope 10 to insufflate carbon dioxide into the gastrointestinal tract through the water storage tank 27 and the endoscope 10, that is, the insufflation conduit for manual insufflation.

Note that when the automatic insufflation is set to ON, the control unit 130 sets the third solenoid valve 124 to the closed state so as to set the insufflation flow rate to a low flow rate of carbon dioxide which can be insufflated from the manual insufflation connector 145 through the second branch conduit 142b. This restricts the insufflation flow rate of the carbon dioxide into the gastrointestinal tract, which increases due to the concurrent use of the automatic insufflation and the manual insufflation, to an appropriate flow rate.

Meanwhile, when the automatic insufflation is set to OFF, the control unit 130 sets the third solenoid valve 124 to the open state so as to set the insufflation flow rate to a high flow rate which is appropriate when only the manual insufflation is performed as the insufflation flow rate of the carbon dioxide which can be insufflated from the manual insufflation connector 145.

Figure 6:
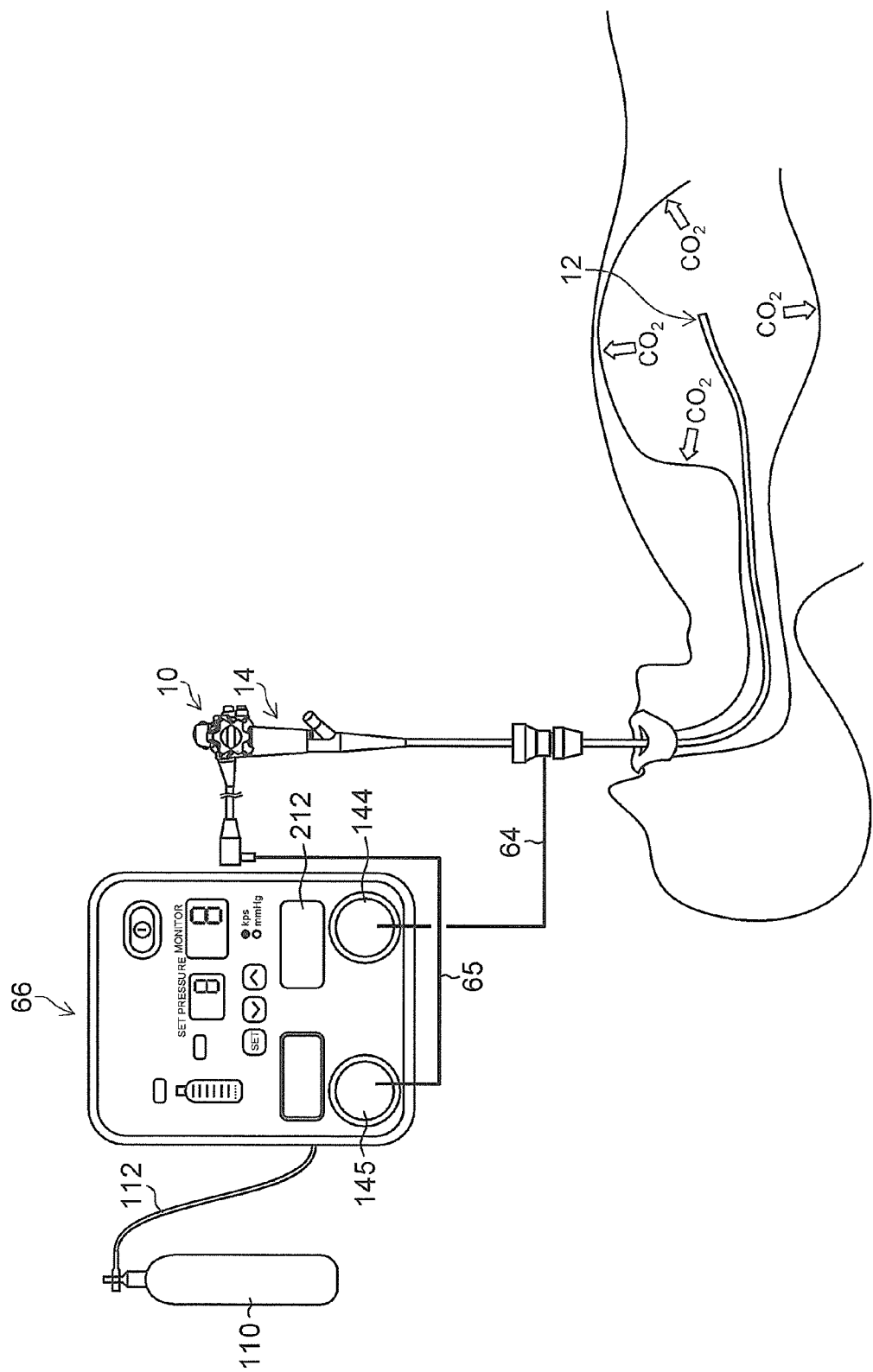
FIG. 6 is a diagram illustrating a usage state of the insufflation system according to the present embodiment.

The insufflation system of the present embodiment configured as above is disposed, for example, as illustrated in FIG. 6, in a state in which the insertion portion 12 of the endoscope 10 is inserted into the gastrointestinal tract of the patient together with the insertion assisting tool 70 in a state of being inserted into the insertion channel 68 of the insertion assisting tool 70. Then, carbon dioxide is insufflated into the gastrointestinal tract from the insufflation apparatus 66 through the water storage tank 27 (unillustrated) and the endoscope 10 or the insertion assisting tool 70.

Note that the gastrointestinal tract into which the insertion portion 12 of the endoscope 10 is inserted includes the esophagus, stomach, small intestine (duodenum, jejunum, ileum), and large intestine (cecum, colon, rectum), and, particularly preferably the stomach, the large intestine, and the like. FIG. 6 illustrates a state in which the insertion portion 12 of the endoscope 10 together with the insertion assisting tool 70 is inserted from the mouth of the patient into the stomach through the esophagus.

Now, the description focuses on the manual insufflation and automatic insufflation modes in the insufflation system of the present embodiment.

Figure 7:
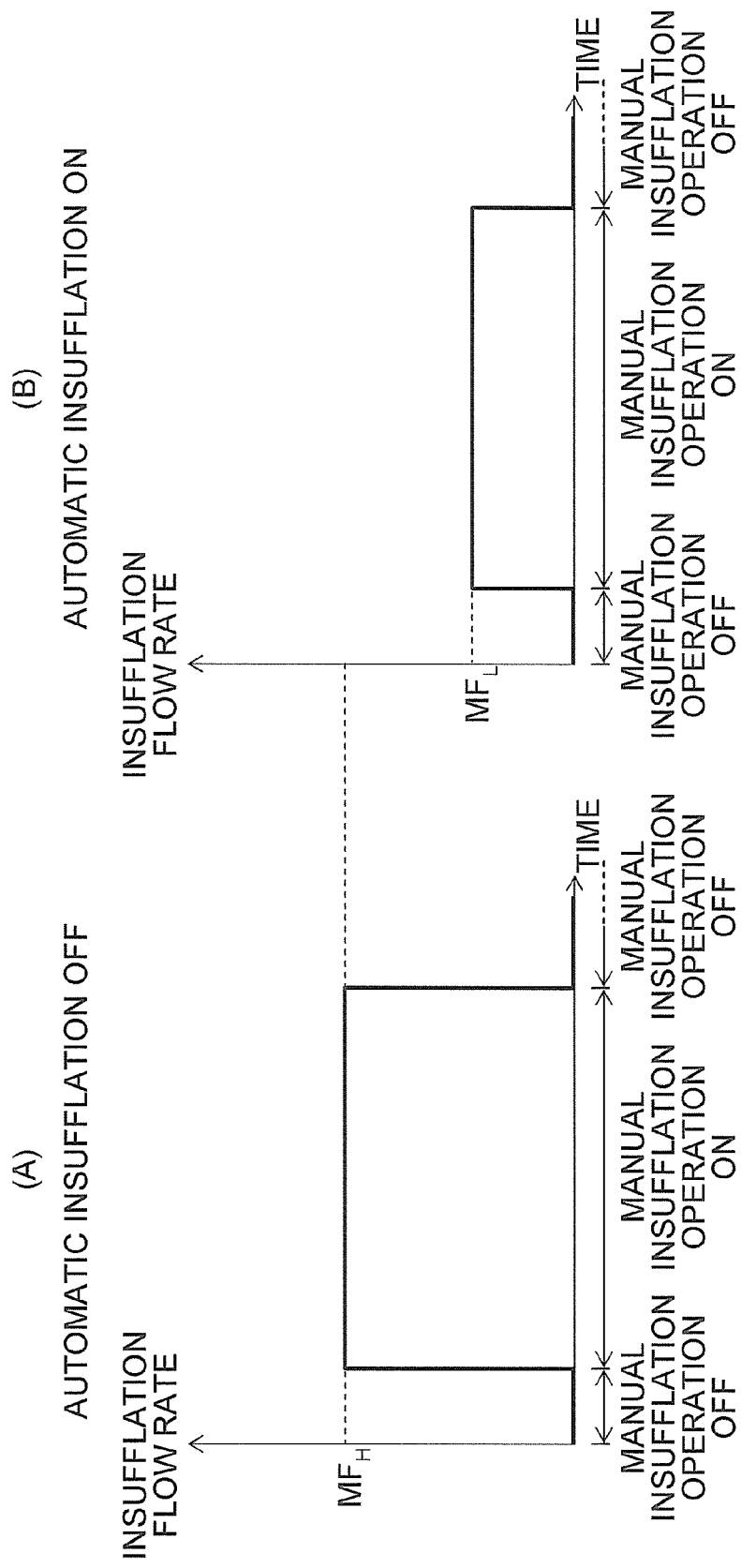
FIG. 7 is an explanatory drawing used to describe an aspect of manual insufflation.

In the manual insufflation mode, for example, as illustrated in Portion (A) in FIG. 7, when the operator sets the vent of the air/water insufflation button 32 of the endoscope 10 to the closed state (manual insufflation operation in progress), carbon dioxide is continuously insufflated into the gastrointestinal tract from the manual insufflation connector 145 through the second branch conduit 142b while the manual insufflation operation is in progress. Then, when the operator opens the vent of the air/water insufflation button 32 of the endoscope 10, the insufflation into the gastrointestinal tract is stopped. The manual insufflation is performed by continuously insufflating carbon dioxide in a manner as described above.

Note that in the manual insufflation mode, the insufflation flow rate (volume of carbon dioxide insufflated per unit time) during actual insufflation can be switched in two stages; a first insufflation flow rate and a second insufflation flow rate, which are different from each other as the control unit 130 switches between the open state and the closed state of the third solenoid valve 124 serving as the flow rate switching device in second branch conduit 142b as illustrated in Portion (A) and Portion (B) in FIG. 7A.

The insufflation flow rates are automatically switched based on whether or not the automatic insufflation is set to ON. When the automatic insufflation is set to OFF, the third solenoid valve 124 is set to the open state. As illustrated in Portion (A) in FIG. 7, the insufflation flow rate is set to the high flow rate, namely, an insufflation flow rate $MF_H$ (for example, in unit of liters/minute), of the first insufflation flow rate and the second insufflation flow rate. Note that the insufflation flow rate $MF_H$ corresponds to the second insufflation flow rate $MF_2$.

The insufflation flow rate $MF_H$ as the high flow rate is a value obtained by adding an insufflation flow rate determined by flow rate restriction by the second orifice 148 in the second branch conduit 142b and an insufflation flow rate determined by flow rate restriction by the third orifice 150 in the bypass conduit 123 of the second branch conduit 142b.

Meanwhile, when the automatic insufflation is set to ON, the third solenoid valve 124 is set to the closed state. As illustrated in Portion (B) in FIG. 7, the insufflation flow rate is set to the low flow rate, namely, an insufflation flow rate $MF_L$, of the first insufflation flow rate and the second insufflation flow rate. Note that the insufflation flow rate $MF_L$ corresponds to the first insufflation flow rate $MF_1$.

The insufflation flow rate $MF_L$ as the low flow rate is equal to the insufflation flow rate determined by flow rate restriction by the second orifice 148 in the second branch conduit 142b.

Those insufflation flow rates are set to be a value less than or equal to an insufflation flow rate MFmax which is assumed not to burden the patient and have the following relationship.

$$MF_L < MF_H \leq MFmax$$

In this way, the insufflation flow rate is switched between the high flow rate and the low flow rate according to whether or not the automatic insufflation is set to ON. Thus, even when the automatic insufflation and manual insufflation are concurrently used, rapid increase of the pressure inside the gastrointestinal tract can be prevented and operability matched to a sense of the operator can be achieved.

In addition, when the automatic insufflation is performed, the insufflation flow rate in the manual insufflation mode is switched to the low flow rate. Thus, even when the automatic insufflation and the manual insufflation are concurrently used, the pressure inside the gastrointestinal tract can be easily finely adjusted by the manual insufflation, and the lumen can be easily maintained in an appropriate expanded condition.

Figure 8:
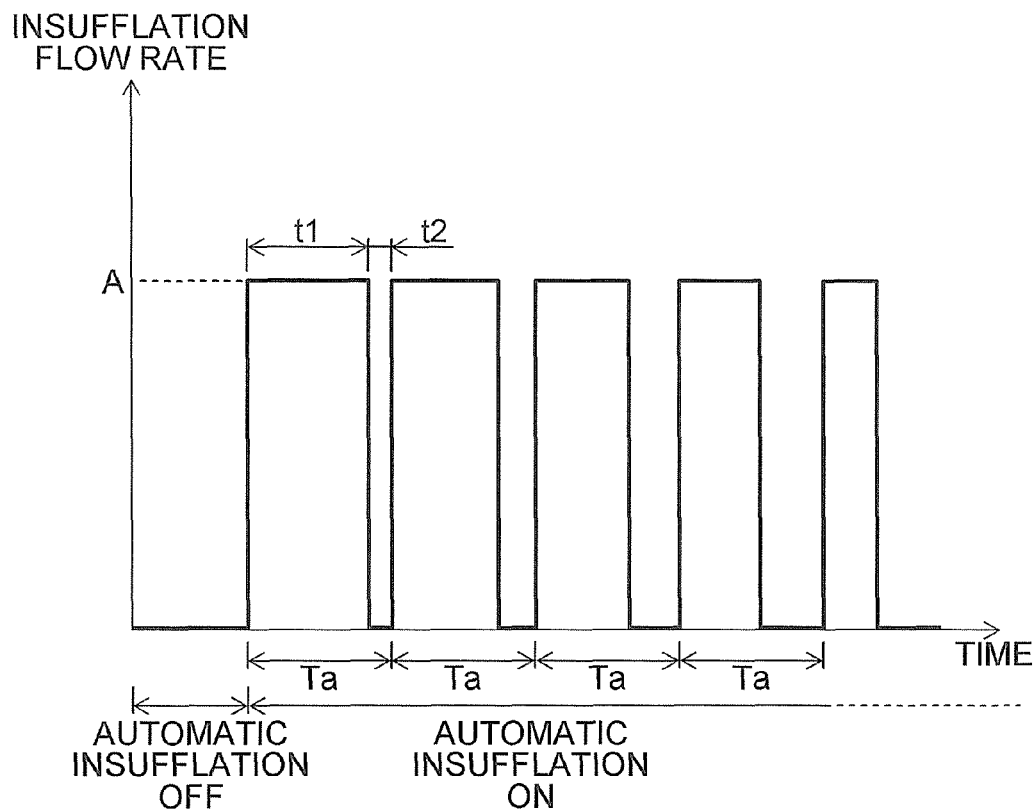
FIG. 8 is an explanatory drawing used to describe an aspect of automatic insufflation.

Meanwhile, as illustrated in FIG. 8, the automatic insufflation is performed by intermittently (pulsewisely) insufflating carbon dioxide.

More specifically, when the operator operates the automatic insufflation button 212 of the insufflation apparatus 66 to switch the setting of the automatic insufflation from OFF to ON, the second solenoid valve 122 is switched every predetermined time between the open state and the closed state while the automatic insufflation is set to ON. Thus, carbon dioxide is intermittently insufflated into the gastrointestinal tract from the automatic insufflation connector 144 through the first branch conduit 142a. When the automatic insufflation is switched to OFF, the second solenoid valve 122 is switched to the closed state, which stops insufflation into the gastrointestinal tract.

Note that even in a state in which the automatic insufflation is set to ON, if the pressure inside the gastrointestinal tract acquired by the pressure detecting device (the third pressure sensor 128 or the fourth pressure sensor 129) is greater than or equal to the set pressure set by the pressure setting portion 210, the second solenoid valve 122 is maintained in the closed state, which stops insufflation into the gastrointestinal tract. This does not mean stopping the automatic insufflation itself, but when the pressure inside the gastrointestinal tract becomes less than the set pressure, intermittent insufflation into the gastrointestinal tract is resumed.

Thus, in the automatic insufflation mode, as illustrated in FIG. 8, the intermittent insufflation is performed by alternately repeating an insufflation step (step for one pulse) of actually continuously insufflating carbon dioxide and a non-insufflation step (pressure detection step) of continuously stopping (pausing) the insufflation.

Note that assuming that one cycle is defined as one repeating unit formed of one insufflation step and one non-insufflation step that follows the one insufflation step, period Ta of the one cycle is set to a preset time. Then, based on the pressure inside the gastrointestinal tract, the ratio (t1/Ta: called duty ratio) of time t1 (time length) of the insufflation step per cycle is set or changed every cycle, and based on the ratio, time t1 of the insufflation step and time t2 of the non-insufflation step are set or changed.

Figure 9:
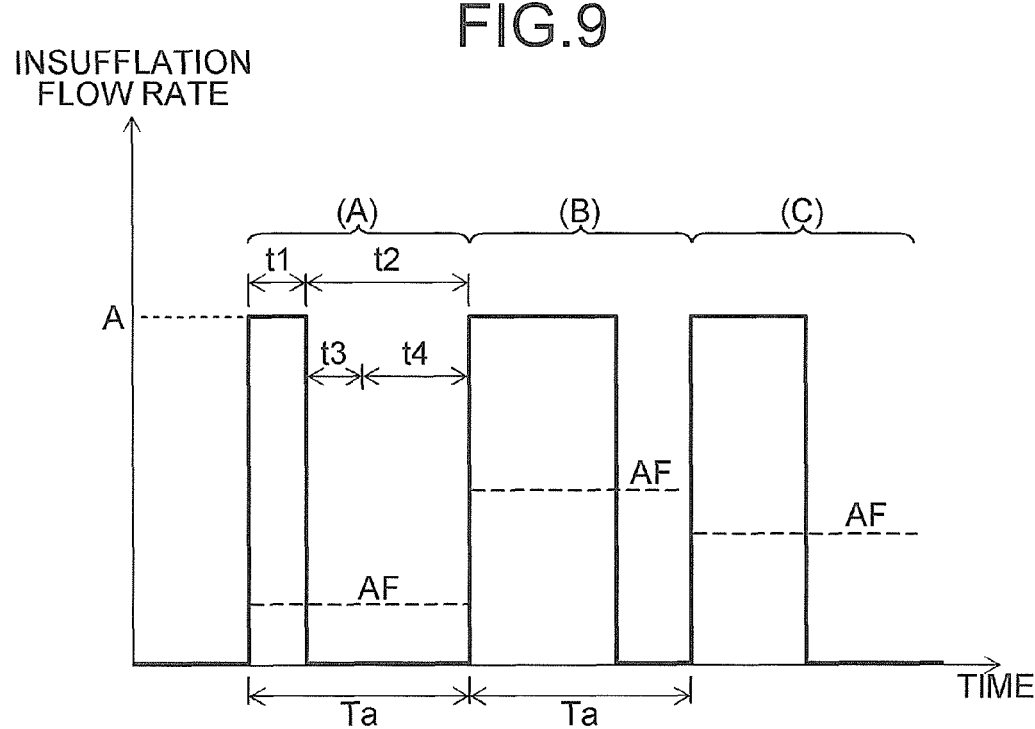
FIG. 9 is an explanatory drawing used to describe an aspect of automatic insufflation.

Here, Portions (A) to (C) in FIG. 9 illustrate three cycles with different duty ratio. Portion (B) in FIG. 9 illustrates a cycle with a maximum duty ratio of the changeable values.

As illustrated FIG. 9, the insufflation flow rate in the insufflation step of each cycle is a substantially constant insufflation flow rate A determined by flow rate restriction due to an effective opening area S1 of the first orifice 146 of the first branch conduit 142a.

Assuming that an average flow rate per cycle is defined as an average value of the insufflation flow rate per cycle including one insufflation step and one non-insufflation step following the one insufflation step, the average flow rate AF is calculated as follows.

$$AF = A \times D, \text{ where } D \text{ is duty ratio.}$$

At this time, the first orifice 146 restricts the insufflation flow rate of the first branch conduit 142a so as to satisfy the condition that the average flow rate AF (average flow rate of the cycle illustrated in Portion (B) in FIG. 9) obtained when the duty ratio D is a maximum value Dmax is less than or equal to the insufflation flow rate $MF_H$ (average flow rate AF≤insufflation flow rate $MF_H$) as the high flow rate in the manual insufflation, and that the average flow rate AF is greater than the insufflation flow rate $MF_L$ (insufflation flow rate $MF_L$<average flow rate AF) as the low flow rate in the manual insufflation, namely, to satisfy the following expression (1).

$$\text{Insufflation flow rate } MF_L < \text{average flow rate } AF \leq \text{insufflation flow rate } MF_H \quad (1)$$

This satisfies the condition: average flow rate AF≤insufflation flow rate $MF_H$ (≤MFmax) when the duty ratio D is any value of the changeable values, thus preventing burdening the patient during automatic insufflation. In addition, when only the automatic insufflation is performed, the insufflation into the lumen can be performed with a sense as close to the manual insufflation. Further, because the average flow rate AF is set to be greater than the insufflation flow rate $MF_L$, even when the manual insufflation is concurrently performed while the automatic insufflation is performed, the pressure inside the lumen can be easily fine-adjusted by the manual insufflation while preventing the pressure inside the gastrointestinal tract from rapidly increasing, and the lumen is easily maintained in an appropriate expanded condition.

In addition, the maximum insufflation flow rate when the automatic insufflation and manual insufflation are concurrently performed is the insufflation flow rate (average flow rate AF+insufflation flow rate $MF_L$) obtained by adding the average flow rate AF when the duty cycle D is the maximum Dmax in the automatic insufflation and the insufflation flow rate $MF_L$ as the low flow rate in the manual insufflation. It is desirable that this insufflation flow rate (average flow rate AF+insufflation flow rate $MF_L$) is also less than or equal to the insufflation flow rate $MF_H$ (that is, less than or equal to MFmax) as the high flow rate in the manual insufflation and satisfies the following expression (2).

$$\text{Average flow rate } AF + \text{insufflation flow rate } MF_L \leq \text{insufflation flow rate } MF_H \quad (2)$$

Thus, even when the manual insufflation is concurrently used during the automatic insufflation, the entire insufflation flow rate (AF+$MF_L$) of the gas insufflated into the gastrointestinal tract is less than or equal to the insufflation flow rate $MF_H$ when only the manual insufflation is performed. Thus, even in the concurrent use of the manual insufflation and the automatic insufflation, the pressure inside the gastrointestinal tract can be prevented from rapidly increasing, and operability matched to a sense of the operator can be achieved.

Meanwhile, the duty ratio D is set based on: a pressure difference ΔP (=Ps−P) between a pressure P inside the gastrointestinal tract acquired by the pressure detecting device (the third pressure sensor 128 or the fourth pressure sensor 129) and a set pressure Ps set by the pressure setting portion 210; and association data associating the pressure difference ΔP with the duty ratio D. The association data is created in advance and stored in a memory or the like of the control unit 130.

If the pressure difference ΔP is less than or equal to a predetermined threshold, the association data is associated such that the greater the pressure difference ΔP, the larger the duty ratio D (that is, the longer the time t1 of the insufflation step). If the pressure difference ΔP exceeds the predetermined threshold, the association data is associated such that the duty ratio D is a predetermined value regardless of the pressure difference ΔP (that is, the time t1 of the insufflation step is a constant time).

Figure 10:
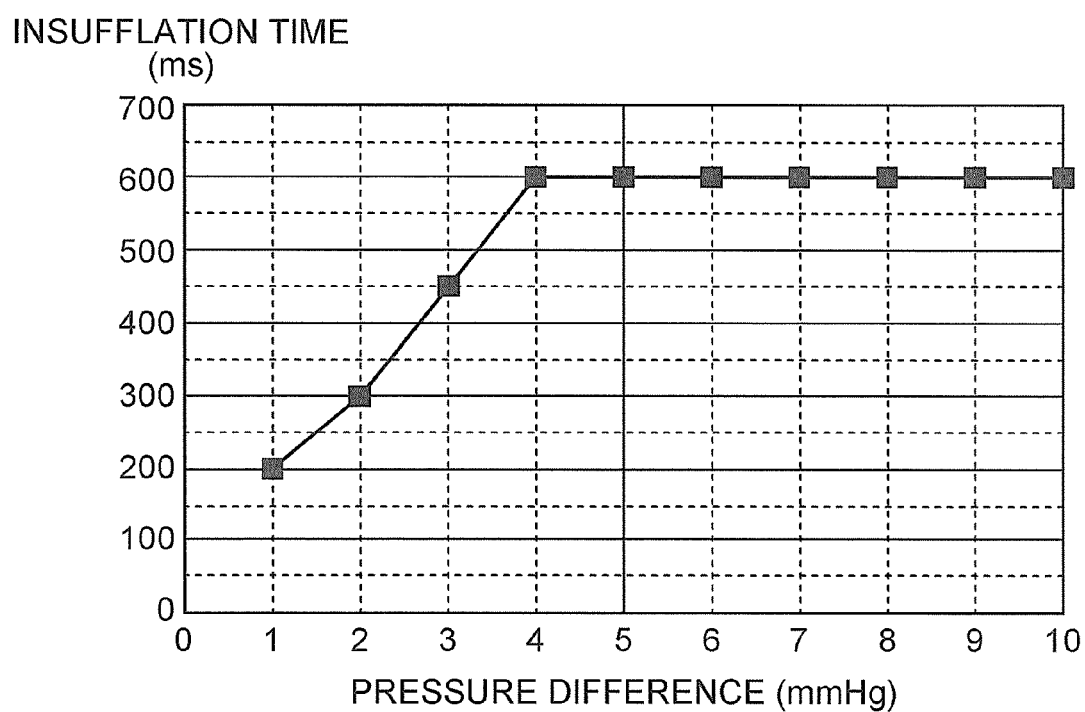
FIG. 10 is a graph illustrating a relationship between a pressure difference and a duty ratio of an insufflation step (time of the insufflation step).

FIG. 10 is a graph illustrating a relationship between the pressure difference ΔP and the time t1 of the insufflation step according to the association. As shown in FIG. 10, if the pressure difference ΔP is less than or equal to a threshold of 4.0 mmHg (about 533 Pa), the time t1 is set such that the greater the pressure difference ΔP, the longer the time t1 of the insufflation step in one cycle. If the pressure difference ΔP exceeds a threshold of 4.0 mmHg (about 533 Pa), the time t1 of the insufflation step in one cycle is set to 600 (ms).

Note that when the pressure P inside the gastrointestinal tract is greater than or equal to the set pressure Ps, insufflation is stopped in the same manner as when the time t1 of the insufflation step is set to 0. Therefore, it is equivalent to setting the duty ratio D to 0 when the pressure difference ΔP has a value less than or equal to 0 (0 and negative values). However, in the present embodiment, the stopping of the insufflation in this case is not performed by setting a value of the duty ratio D, and hence the changeable values of the duty ratio D is assumed not to include 0. In addition, the pressure difference ΔP is only assumed to be greater than 0.

Specifically, the duty ratio D is changed in the range from 0.1 to 0.7, and accordingly the time t1 of the insufflation step is changed in the range from Ta×0.1 to Ta×0.7.

For example, assuming that the period Ta of one cycle is 6/7 second, the time t1 of the insufflation step is changed in the range from 0.6/7 to 0.6 second.

Note that the time t2 of the non-insufflation step in the automatic insufflation has a period of (6/7 minus 0.6) second even in the minimum time (time assuming a maximum duty ratio D of 0.7). As illustrated in Portion (A) in FIG. 9, a predetermined time (wait time) t3, which is a time since immediately after the end of insufflation step within the time t2 of the non-insufflation step, is a time of waiting for the pressure inside the gastrointestinal tract to be stabilized. In the remaining time (measurement time) t4, which is a time after the wait time t3 has elapsed, the pressure inside the gastrointestinal tract is detected by the pressure detecting device (the third pressure sensor 128 or the fourth pressure sensor 129).

Thus, in the automatic insufflation, insufflation is intermittently performed and the pressure inside the gastrointestinal tract is detected while the insufflation is stopped, and hence the automatic insufflation into the gastrointestinal tract is stabilized.

Note that the wait time t3 may be any value as long as the time t3 is shorter than at least the time t2 of the non-insufflation step, and may be changed according to the time t2 of the non-insufflation step.

Now, the operation of the insufflation apparatus 66 of the present embodiment will be described with reference to the flowchart in FIGS. 11 and 12.

Figure 11:
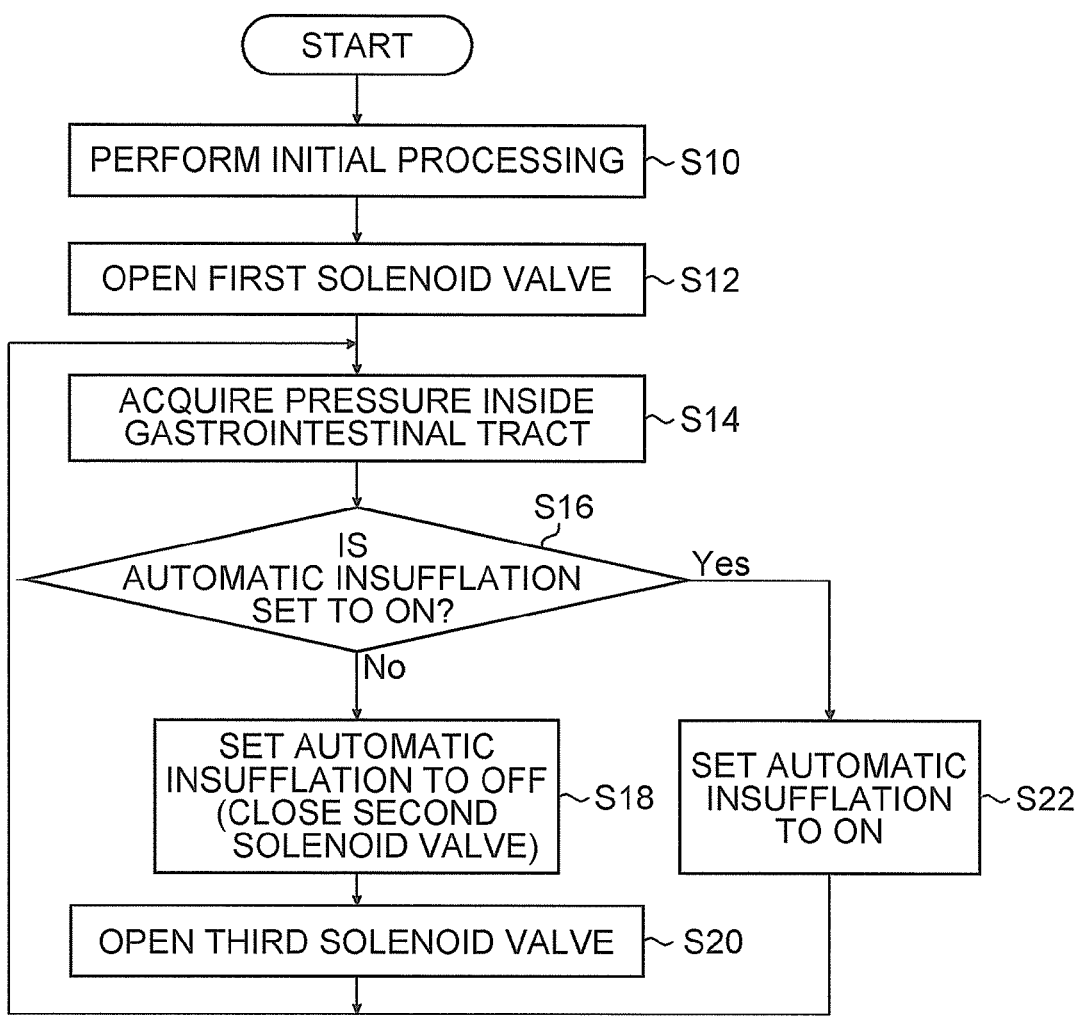
FIG. 11 is a flowchart illustrating an example of an operation of the insufflation apparatus.

FIG. 11 is a flowchart illustrating an example of the operation of the insufflation apparatus 66.

First, the power switch 132 of the insufflation apparatus 66 is turned on, and then initial processing such as operation confirmation of each portion is performed (Step S10).

Then, as pre-processing, the control unit 130 places the first solenoid valve 120 in an open state so as to place the internal conduit 142 in a communication state (Step S12). This enables manual insufflation of carbon dioxide into the gastrointestinal tract according to the operation of the air/water insufflation button 32 of the endoscope 10. Subsequently, the manual insufflation is performed according to the operation of the operator without the need for the control unit 130 to perform special processing until the control unit 130 switches the first solenoid valve 120 to a closed state, such as when the power switch 132 is turned off.

Then, the control unit 130 acquires a pressure inside the gastrointestinal tract (Step S14). The detection of the pressure inside the gastrointestinal tract is performed by the third pressure sensor 128 or the fourth pressure sensor 129 as the pressure detecting device. The detection result is outputted to the control unit 130. The control unit 130 calculates the actual pressure inside the gastrointestinal tract by correcting the pressure loss occurring from the pressure detection position to within the gastrointestinal tract. Thus acquired pressure of the gastrointestinal tract is displayed on the pressure display portion 208.

Then, the control unit 130 determines whether or not the automatic insufflation is set to ON (Step S16). As described above, based on the operation of the automatic insufflation button 212, a determination is made as to whether or not the automatic insufflation is set to ON. Note that it is assumed that the automatic insufflation is set to OFF at the time of the start of the insufflation apparatus 66, but the present disclosure is not limited to this.

Then, when the determination result is "NO" in Step S16, that is, when it is determined that the automatic insufflation is not set to ON (the automatic insufflation is determined to be set to OFF), the process moves to Step S18, where the control unit 130 places the second solenoid valve 122 in the closed state so as to place the first branch conduit 142a in a non-communication state. If the second solenoid valve 122 has been in the closed state, the closed state is maintained. As a result, the automatic insufflation into the gastrointestinal tract is turned off (stopped).

Then, the control unit 130 places the third solenoid valve 124 in the open state so as to place bypass conduit 123 of the second branch conduit 142b in a communication state (Step S20). If the third solenoid valve 124 has been in the open state, the open state is maintained. As a result, the insufflation flow rate into the gastrointestinal tract by the manual insufflation is set to the insufflation flow rate $MF_H$ as the high flow rate. Then, the process returns to Step S14 and repeats the process in and after Step S14.

Meanwhile, when the determination result is "YES" in Step S16, that is, when it is determined that the automatic insufflation is set to ON, the process moves to Step S22, where the control unit 130 performs automatic insufflation control processing to be described below to turn on (execute) the automatic insufflation into the gastrointestinal tract. Then, the process returns to Step S14 and repeats the process in and after Step S14.

Thus, the control unit 130 repeats the process in and after Step S14. When the power switch 132 is operated to set to OFF, the control unit 130 places the first solenoid valve 120 in the closed state to stop operation. Note that the power switch 132 is used to switch the first solenoid valve 120 between the open state and the closed state, but a predetermined operation member may be used for switching.

Now, the description focuses on the automatic insufflation control processing.

Figure 12:
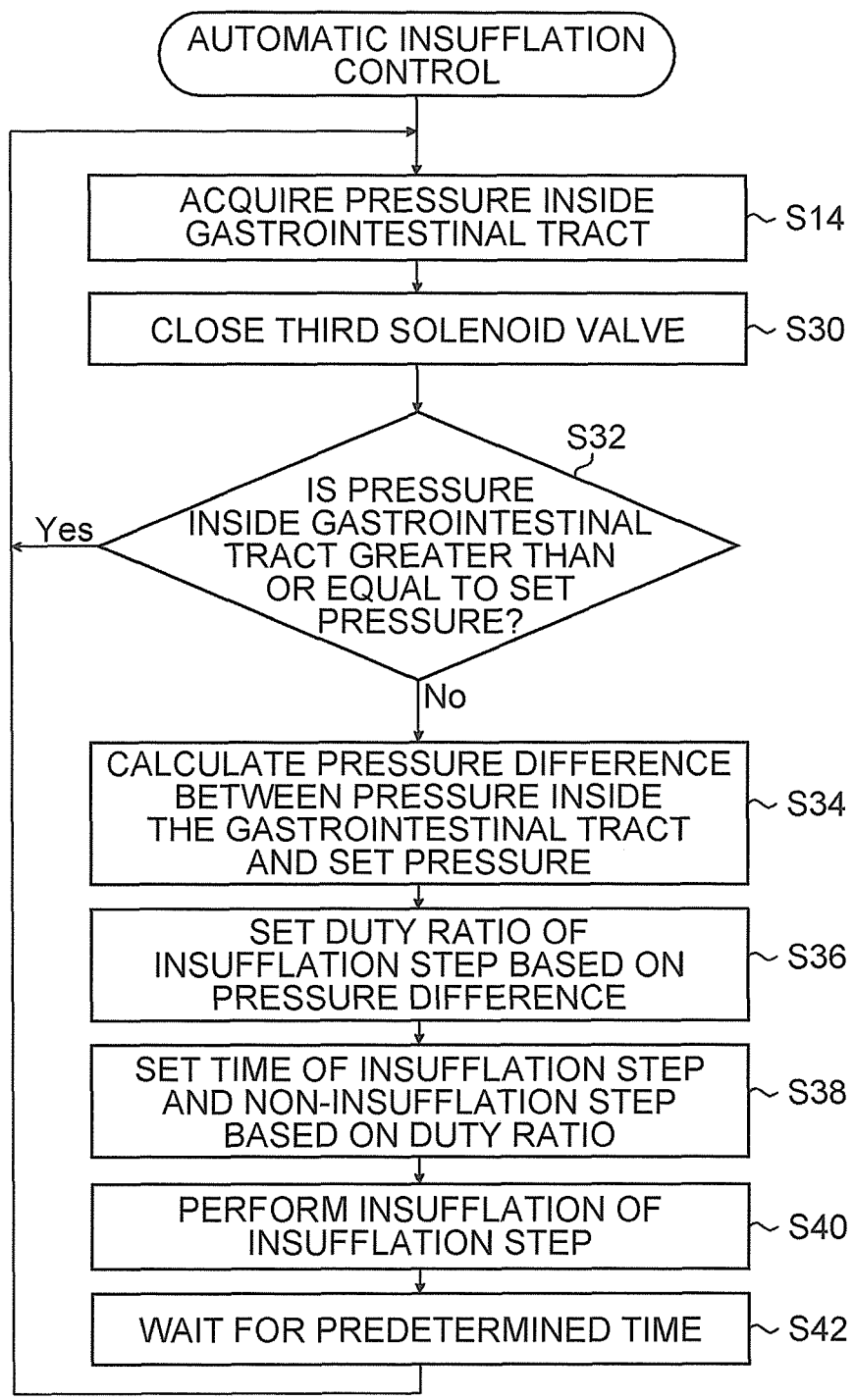
FIG. 12 is a flowchart illustrating a processing procedure for automatic insufflation control.

While the automatic insufflation "ON" is set, the determination result is "YES" in Step S16 in FIG. 11, and then the processes in Step S14 and Step S22 are repeated so that the automatic insufflation control processing like the flowchart of FIG. 12 is repeated. Note that FIG. 12 omits the determination process in Step S16, and the process of placing the first solenoid valve 120 in the closed state and stopping the operation of the insufflation apparatus 66 according to the power switch 132 being set to "OFF", which are assumed to be appropriately performed.

First, the control unit 130 acquires the pressure inside the gastrointestinal tract (Step S14). Then, the control unit 130 places the third solenoid valve 124 in the closed state so as to place the bypass conduit 123 of the second branch conduit 142b in the non-communication state (Step S30). If the third solenoid valve 124 has been in the closed state, the closed state is maintained. As a result, the insufflation flow rate inside the gastrointestinal tract by the manual insufflation is restricted to the insufflation flow rate $MF_L$ as the low flow rate.

Then, the control unit 130 compares the pressure P inside the gastrointestinal tract acquired in Step S14 with the set pressure Ps preset by the pressure setting portion 210 to determine whether or not the pressure P inside the gastrointestinal tract is greater than or equal to the set pressure Ps (Step S32).

Then, when the determination result is "YES" in Step S32, that is, when it is determined that the pressure inside the gastrointestinal tract is greater than or equal to the set pressure, the control unit 130 returns to Step S14 without performing the following process, and repeats the process in Step S14. Note that at this time, the second solenoid valve 122 is maintained in the closed state and the insufflation into the gastrointestinal tract is stopped.

Meanwhile, when the determination result is "NO" in Step S32, that is, when it is determined that the pressure P inside the gastrointestinal tract is less than the set pressure Ps, the process moves to Step S34, where the control unit 130 calculates the pressure difference ΔP which is a difference between the pressure P inside the gastrointestinal tract and the set pressure Ps (set pressure Ps-pressure P inside the gastrointestinal tract) (Step S34).

Then, based on the pressure difference ΔP calculated in Step S34, the control unit 130 sets the duty ratio D of the insufflation step in the automatic insufflation using the association data stored in the memory in advance as described above (Step S36).

Thus, when the pressure difference ΔP is less than or equal to a predetermined threshold, the duty ratio D is set such that the greater the pressure difference ΔP, the larger the duty ratio D of the insufflation step. When the pressure difference ΔP exceeds the predetermined threshold, the duty ratio D is set to a predetermined value (maximum value Dmax) regardless of the pressure difference ΔP.

Then, the control unit 130 sets (calculates) the time (length) t1 of the insufflation step and the time (length) t2 of the non-insufflation step based on the duty ratio D of the insufflation step set in Step S34 (Step S38). Specifically, the time t1 of the insufflation step is obtained by multiplying the period Ta of one cycle with the duty ratio D of the insufflation step, and the time t2 of the non-insufflation step is obtained by subtracting the time t1 of the insufflation step from the period Ta of one cycle.

Then, when the time t1 of the insufflation step set in Step S38 has elapsed since the second solenoid valve 122 is switched from the closed state to the open state, the control unit 130 switches the second solenoid valve 122 to the closed state (Step S40). Thus, the control unit 130 performs insufflation into the gastrointestinal tract while the second solenoid valve 122 is in the open state.

Then, after switching the second solenoid valve 122 to the closed state in Step S40, the control unit 130 waits until a predetermined wait time t3 has elapsed (Step S42). The pressure inside the gastrointestinal tract is stabilized during the wait time t3.

When the wait time t3 has elapsed in Step S42, the process returns to Step S14, where the control unit 130 acquires the pressure inside the gastrointestinal tract.

Then, before the elapsed time since the second solenoid valve 122 has been switched to the closed state in Step S40 reaches the time t2 of the non-insufflation step, the control unit 130 performs the processes from Step S30 to Step S38. Except for a case where the determination result is "YES" in Step S32, the control unit 130 sets the time t1 of the insufflation step and the time t2 of the non-insufflation step based on the newly acquired pressure inside the gastrointestinal tract.

Then, at the same time when the previously set time t2 of the non-insufflation step has elapsed (time t2 has elapsed after the lapse of the wait time t3), the control unit 130 performs a process of the insufflation step in Step S38 to insufflate into the gastrointestinal tract.

Thus, the pressure inside the gastrointestinal tract is maintained to the set pressure by repeating the automatic insufflation control processing.

The present embodiment has been described by taking an example of the case in which carbon dioxide is applied as the gas insufflated into the gastrointestinal tract, but the gas insufflated into the gastrointestinal tract is not limited to the carbon dioxide, and for example, another gas such as helium gas may be used.

Hereinbefore, the insufflation apparatus according to the present disclosure has been described in detail, but the present disclosure is not limited to the above embodiment and it should be understood that various improvements and modifications can be made to the present disclosure without departing from the spirit and scope of the present disclosure. Hereinafter, some modifications will be described.

[First Modification]

Figure 13:
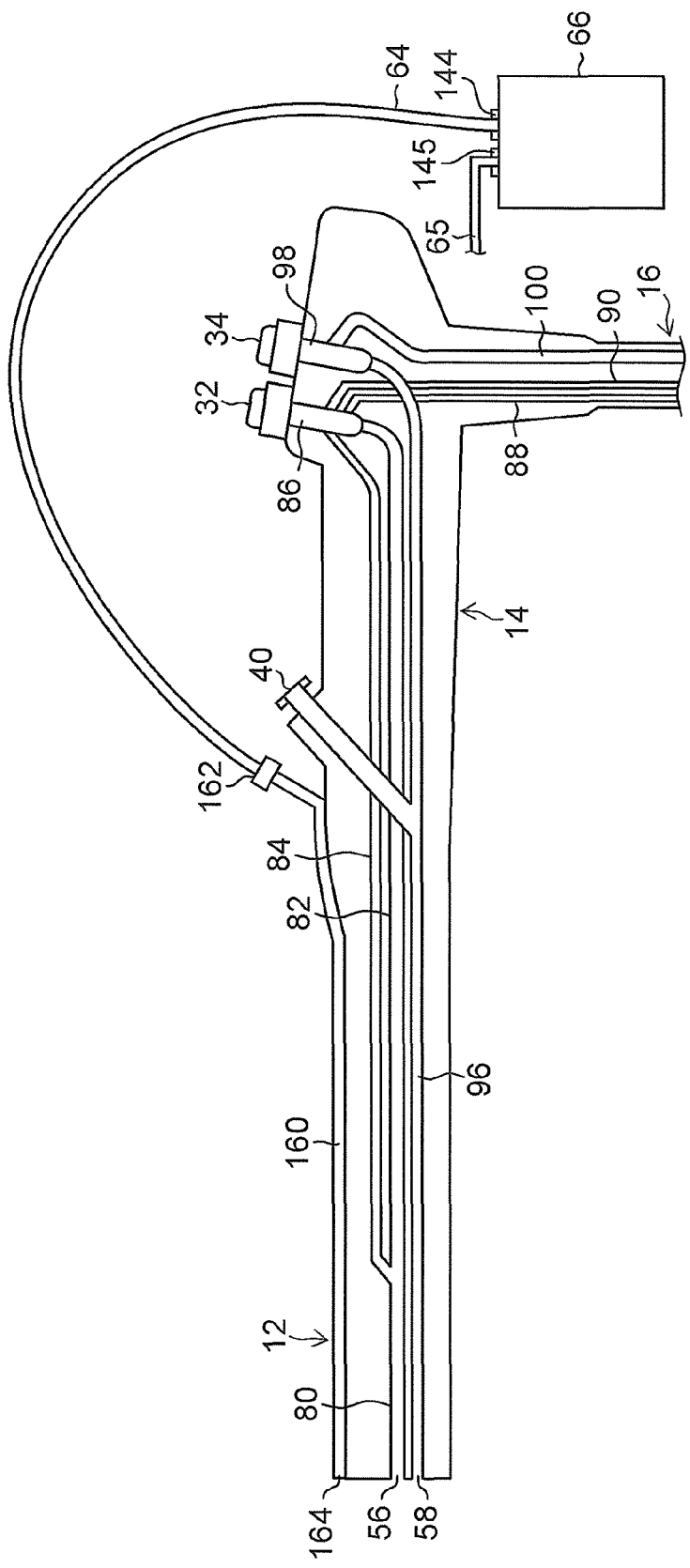
FIG. 13 is a schematic diagram schematically illustrating a conduit configuration of an endoscope as a first modification.

FIG. 13 is a schematic diagram schematically illustrating a conduit configuration of an endoscope as a first modification. In FIG. 13, the same reference numerals or characters are assigned to the members common or similar to those in FIG. 3, and the description thereof is omitted.

According to the first modification as illustrated in FIG. 13, part of the insufflation conduit for insufflating carbon dioxide into the gastrointestinal tract by automatic insufflation includes an external tube 160 which is an external instrument disposed along a longitudinal direction of the insertion portion 12 of the endoscope 10. The external tube 160 is fixed to an outer periphery of the insertion portion 12 of the endoscope 10 by a fixing device (unillustrated) such as a tape. The proximal end side of the external tube 160 includes a gas supply port 162, to which one end of the automatic insufflation tube 64 is detachably connected. The gas supply port 162 communicates with a distal end opening portion 164 of the external tube 160 through a conduit (unillustrated) formed inside the external tube 160. Thus, carbon dioxide is supplied from the insufflation apparatus 66 to the gas supply port 162, passing through the conduit inside the external tube 160, and is insufflated from the distal end opening portion 164 into the gastrointestinal tract.

According to the first modification, the automatic insufflation can be performed even in a gastrointestinal tract deep portion into which it is difficult to insert the insertion assisting tool 70.

[Second Modification]

Figure 14:
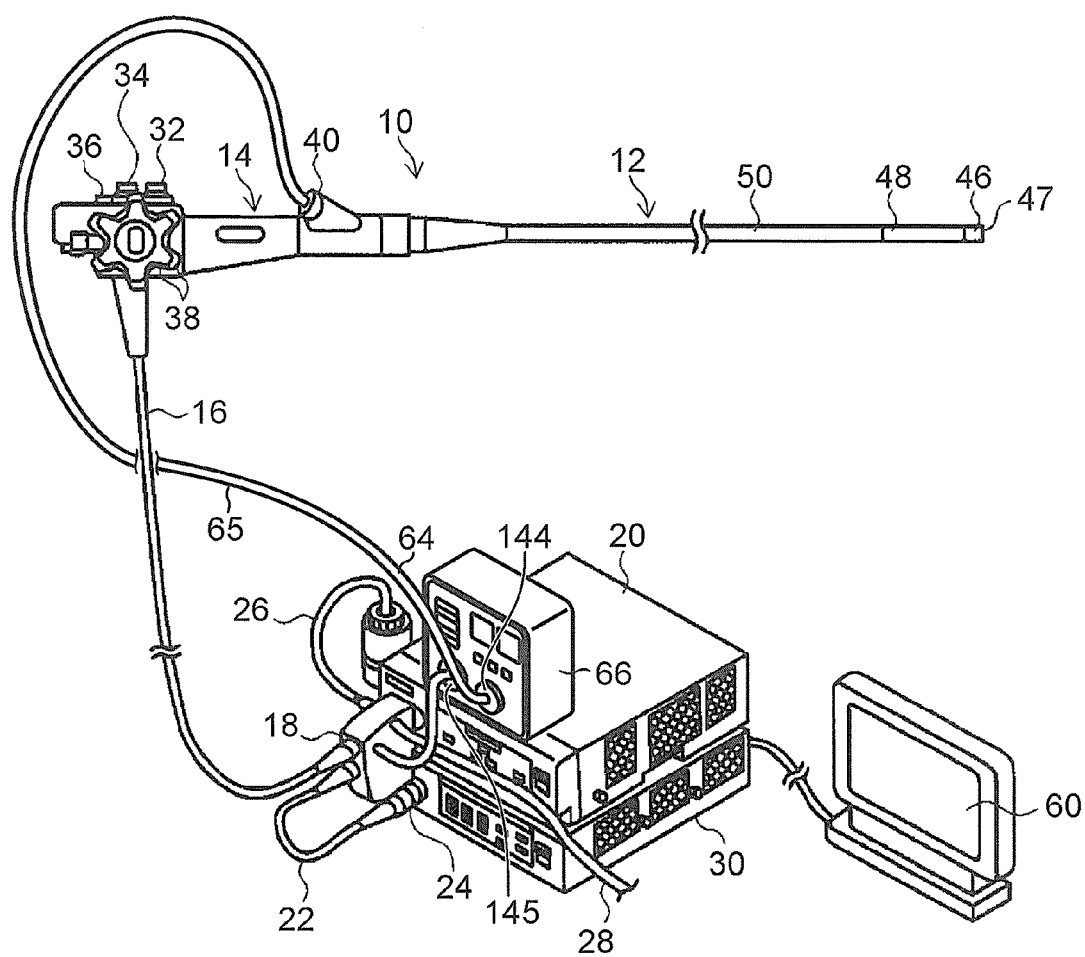
FIG. 14 is an entire configuration diagram illustrating a schematic configuration of an endoscope system as a second modification.
Figure 15:
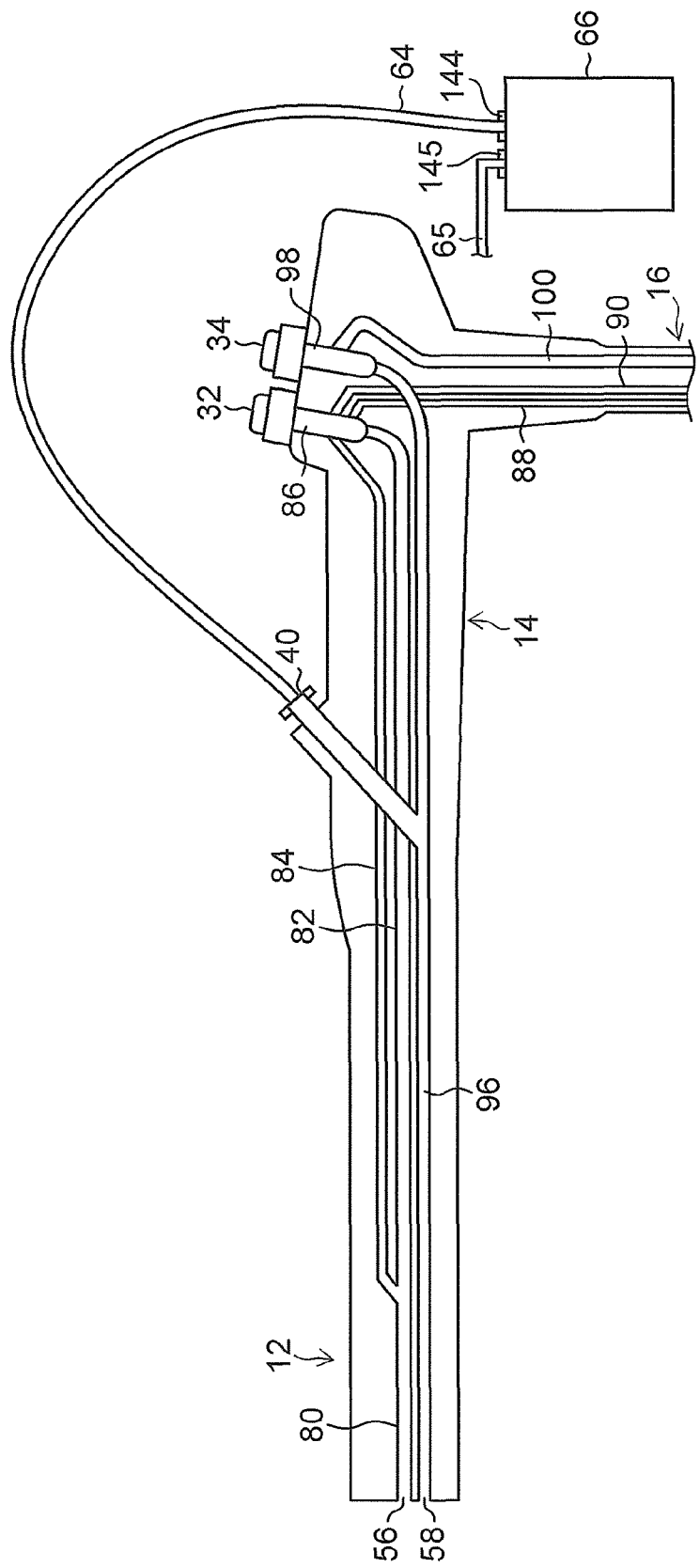
FIG. 15 is a conduit configuration diagram illustrating an internal configuration of the endoscope illustrated in FIG. 14.

FIG. 14 is an entire configuration diagram illustrating a schematic configuration of an endoscope system as a second modification. FIG. 15 is a conduit configuration diagram illustrating an internal configuration of the endoscope illustrated in FIG. 14. In FIGS. 14 and 15, the same reference numerals or characters are assigned to the members common or similar to those in FIGS. 1 and 3, and the description thereof is omitted.

According to the second modification as illustrated in FIGS. 14 and 15, part of the insufflation conduit for insufflating carbon dioxide into the gastrointestinal tract by automatic insufflation includes the forceps tube 96 of the endoscope 10.

One end of the automatic insufflation tube 64 is detachably connected to the forceps insertion portion 40, and the other end of the automatic insufflation tube 64 communicates with the automatic insufflation connector 144 of the insufflation apparatus 66. Thus, carbon dioxide is supplied from the automatic insufflation connector 144 of the insufflation apparatus 66 into the automatic insufflation tube 64, passing through the forceps insertion portion 40 and the forceps tube 96, and is insufflated from the forceps port 58.

The second modification allows even the endoscope system without using the insertion assisting tool 70 to perform the automatic insufflation without the need to provide a special conduit.

[Third Modification]

Figure 16:
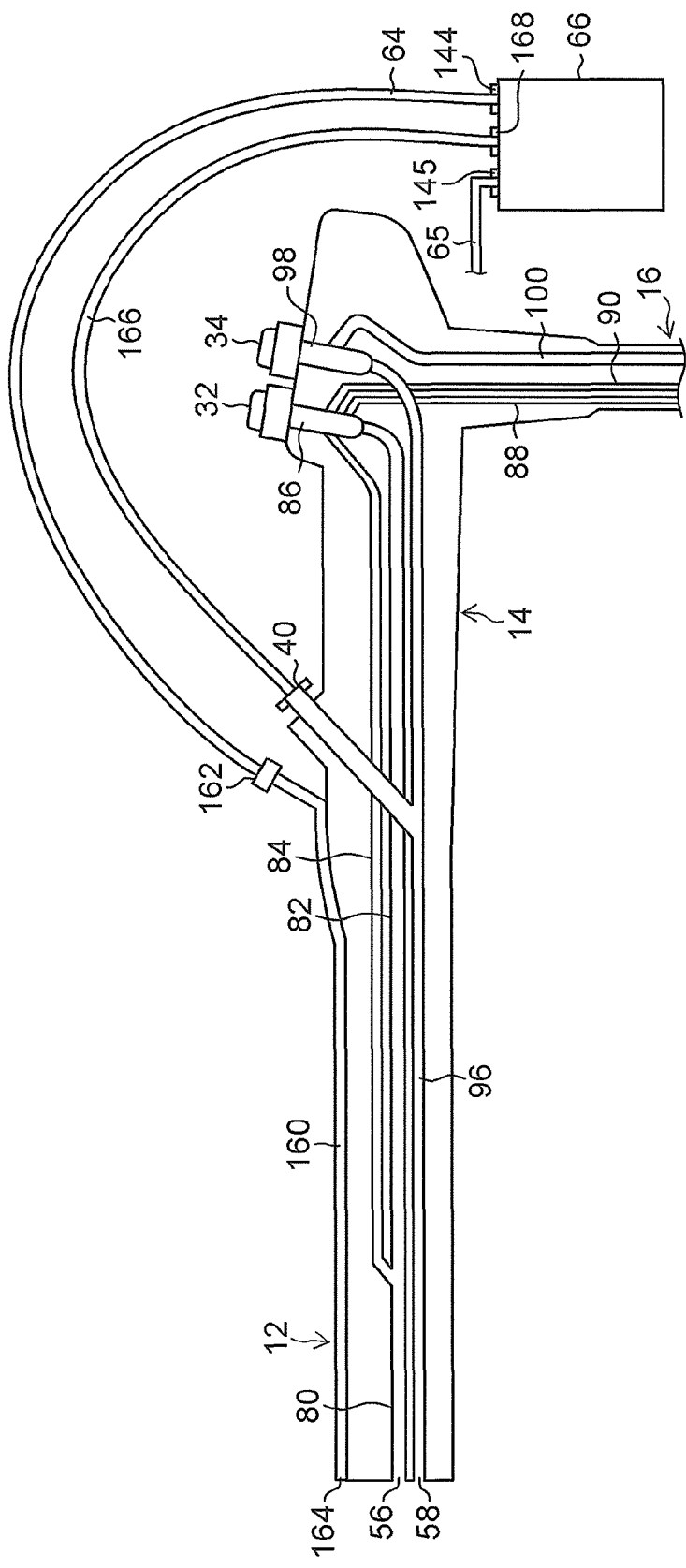
FIG. 16 is a schematic diagram schematically illustrating a conduit configuration of an endoscope as a third modification.
Figure 17:
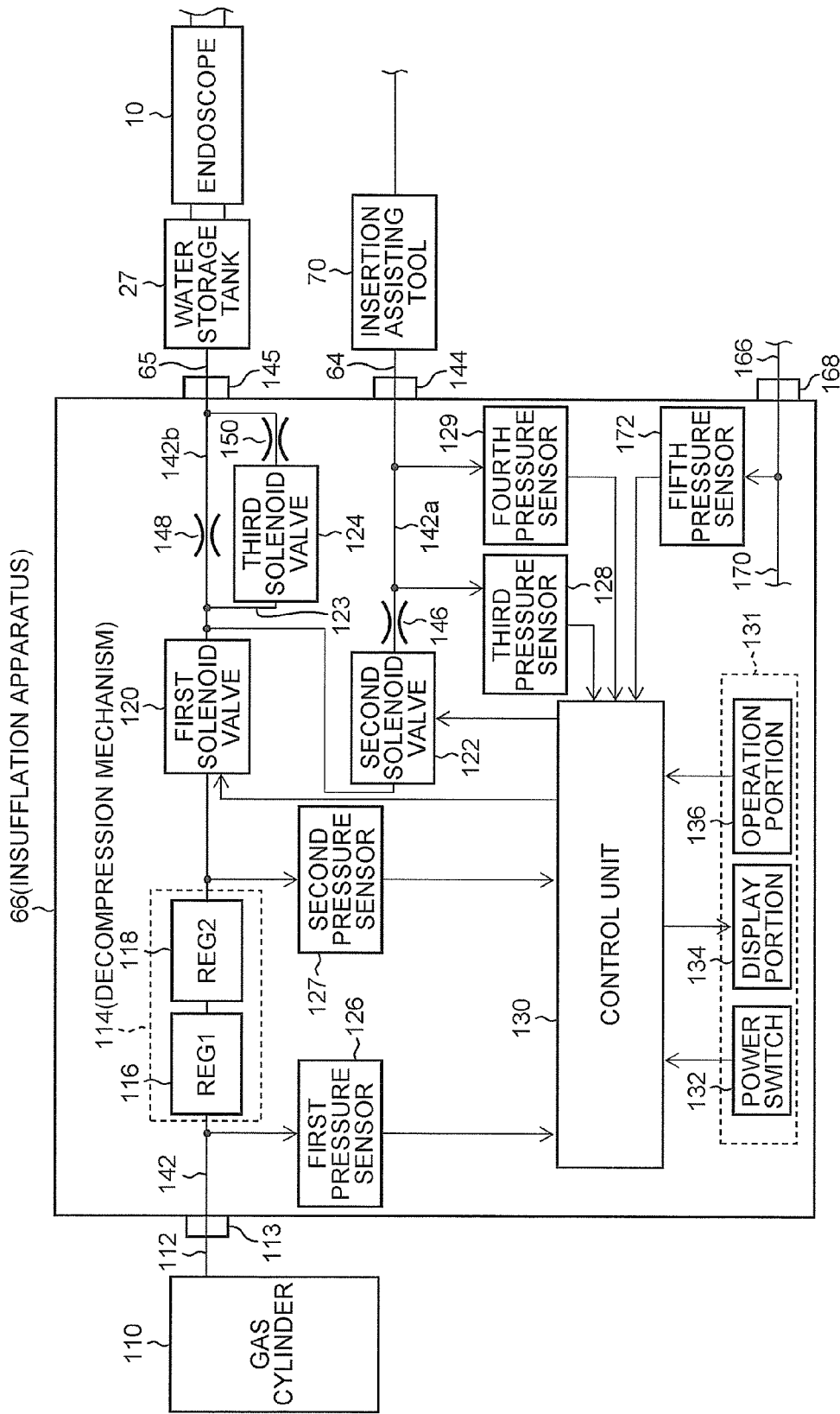
FIG. 17 is a block diagram illustrating a configuration of an insufflation apparatus as a third modification.

FIG. 16 is a schematic diagram schematically illustrating a conduit configuration of an endoscope as a third modification. FIG. 17 is a block diagram illustrating a configuration of an insufflation apparatus as a third modification. In FIGS. 16 and 17, the same reference numerals or characters are assigned to the members common or similar to those in FIGS. 3 and 4, and the description thereof is omitted.

The third modification is the same as the first modification in that the external tube 160 externally provided along the longitudinal direction is configured in the insertion portion 12 of the endoscope 10 as part of the insufflation conduit, but is different from the first modification in that a pressure detecting conduit for detecting the pressure inside the gastrointestinal tract is configured separately from the insufflation conduit.

Specifically, as illustrated in FIG. 16, one end of the pressure detecting tube 166 is detachably connected to the forceps insertion portion 40 of the endoscope 10, and the other end of the pressure detecting tube 166 is connected to the pressure detecting connector 168 of the insufflation apparatus 66.

As illustrated in FIG. 17, inside the insufflation apparatus 66, an internal conduit 170 is provided. The internal conduit 170 is in a non-communication state with respect to the internal conduit 142 and the branch conduits 142a and 142b. One end of the internal conduit 170 is connected to the pressure detecting connector 168. A fifth pressure sensor 172 is connected to the internal conduit 170. The fifth pressure sensor 172 detects a pressure inside the gastrointestinal tract through a pressure detecting conduit (the internal conduit 170, the pressure detecting tube 166, and the forceps tube 96) configured separately from the insufflation conduit (the first branch conduit 142a, the automatic insufflation tube 64, and the external tube 160) for supplying carbon dioxide into the gastrointestinal tract.

According to the third modification, when the pressure inside the gastrointestinal tract is detected, the pressure inside the gastrointestinal tract is detected through the pressure detecting conduit configured separately from the insufflation conduit for insufflating carbon dioxide into the gastrointestinal tract. This makes it possible to detect the pressure inside the gastrointestinal tract in a stable manner and with high precision without being affected by the insufflation into the gastrointestinal tract. This accordingly makes it possible to set the pressure inside the gastrointestinal tract to a target pressure in a simple manner and with high precision.

Note that the third modification is configured such that part of the insufflation conduit includes the external tube 160, and part of the pressure detecting conduit includes the forceps tube 96, but without being limited to this, for example, the third modification may be reversely configured such that part of the insufflation conduit includes the forceps tube 96, and part of the pressure detecting conduit includes the external tube 160. In other words, one end of the automatic insufflation tube 64 may be connected to the forceps insertion portion 40, and one end of the pressure detecting tube 166 may be connected to the gas supply port 162 of the external tube 160.

Alternatively, when a plurality of treatment tool channels (treatment tool insertion channels) are provided in the insertion portion 12 of the endoscope 10, one treatment tool channel may be configured as part of the insufflation conduit, and the other treatment tool channel may be configured as part of the pressure detecting conduit.

Alternatively, like the embodiment in FIG. 1, when the insertion assisting tool 70 is used, the insertion channel 68 of the insertion assisting tool 70 may be configured as part of the insufflation conduit, and the forceps tube 96 which is an internal conduit of the endoscope 10 may be configured as part of the pressure detecting conduit. Still alternatively, this may be reversely configured.

What is claimed is:

1. An insufflation system which insufflates a gas supplied from a gas supply source into a lumen of a living body, the insufflation system comprising:
    a first insufflation conduit through which the gas is automatically insufflated into the lumen;
    a second insufflation conduit through which the gas is insufflated into the lumen by manual operation;
    a pressure sensor configured to detect a pressure inside the lumen;
    a first solenoid valve configured to control an insufflation flow rate of the first insufflation conduit;
    a second solenoid valve configured to control an insufflation flow rate of the second insufflation conduit; and
    a control unit configured to control operations of the first solenoid valve and the second solenoid valve;
    wherein the control unit controls the insufflation flow rate of the first insufflation conduit based on a pressure difference between the pressure detected by the pressure sensor and a preset set pressure and determines whether or not the gas is insufflated through one or both of the first insufflation conduit and the second insufflation conduit,
    when a determined result is determined that the gas is insufflated through both of the first insufflation conduit and the second insufflation conduit, the second solenoid valve is controlled, and the insufflation flow rate of the gas insufflated through the second insufflation conduit is set as a first insufflation flow rate $MF_1$,
    when a determined result is determined that the gas is not insufflated through the first insufflation conduit, the second solenoid valve is controlled, and the insufflation flow rate of the gas insufflated through the second insufflation conduit is set as a second insufflation flow rate $MF_2$ greater than the first insufflation flow rate $MF_1$.

2. The insufflation system according to claim 1, wherein when AF is defined as the insufflation flow rate of the gas insufflated through the first insufflation conduit, a following expression is satisfied $$MF_1 < AF \leq MF_2$$

3. The insufflation system according to claim 1, wherein when AF is defined as the insufflation flow rate of the gas insufflated through the first insufflation conduit, a following expression is satisfied $$MF_1 + AF \leq MF_2$$

4. The insufflation system according to claim 1, wherein the control unit alternately repeats an insufflation step of insufflating the gas through the first insufflation conduit, and a pressure detection step of stopping insufflating the gas through the first insufflation conduit and detecting the pressure inside the lumen by the pressure sensor.

5. An insufflation apparatus which insufflates a gas supplied from a gas supply source into a lumen of a living body, the insufflation apparatus comprising:
- a first connector, configured to be connected to a first insufflation conduit through which the gas is automatically insufflated into the lumen;
- a second connector, configured to be connected to a second insufflation conduit through which the gas is insufflated into the lumen by manual operation;
- a pressure sensor configured to detect a pressure inside the lumen;
- a first solenoid valve configured to control an insufflation flow rate of the first insufflation conduit;
- a second solenoid valve configured to control an insufflation flow rate of the second insufflation conduit; and
- a control unit configured to control operations of the first solenoid valve and the second solenoid valve;

wherein the control unit controls the insufflation flow rate of the gas supplied to the first insufflation conduit based on a pressure difference between the pressure detected by the pressure sensor and a preset set pressure and determines whether or not the gas is supplied to insufflated through one or both of the first insufflation conduit and the second insufflation conduit, when a determined result is determined that the gas is insufflated through both of the first insufflation conduit and the second insufflation conduit, the second solenoid valve is controlled, and the insufflation flow rate of the gas insufflated through the second insufflation conduit is set as a first insufflation flow rate $MF_1$, when a determined result is determined that the gas is not insufflated through the first insufflation conduit, the second solenoid valve is controlled, and the insufflation flow rate of the gas insufflated through the second insufflation conduit is set as a second insufflation flow rate $MF_2$ greater than the first insufflation flow rate $MF_1$.

* * * * *